United States Patent
Harada

[11] Patent Number: 6,106,530
[45] Date of Patent: Aug. 22, 2000

[54] STENT DELIVERY DEVICE

[75] Inventor: Kinya Harada, Shizuoka-ken, Japan

[73] Assignee: Terumo Kabushiki Kaisha, Tokyo, Japan

[21] Appl. No.: 09/010,590

[22] Filed: Jan. 22, 1998

[30] Foreign Application Priority Data

Jan. 24, 1997 [JP] Japan ................................. 9-026135

[51] Int. Cl.$^7$ .................................................. A61F 11/00
[52] U.S. Cl. .......................................... 606/108; 606/195
[58] Field of Search ........................... 606/108, 195, 606/194, 198; 604/96

[56] References Cited

U.S. PATENT DOCUMENTS

| | | |
|---|---|---|
| Re. 34,633 | 6/1994 | Sos et al. .................................. 604/96 |
| 4,684,363 | 8/1987 | Ari et al. . |
| 4,733,665 | 3/1988 | Palmaz . |
| 4,739,762 | 4/1988 | Palmaz . |
| 4,762,128 | 8/1988 | Rosenbluth . |
| 4,776,337 | 10/1988 | Palmaz . |
| 4,893,623 | 1/1990 | Rosenbluth . |
| 4,917,088 | 4/1990 | Crittenden . |
| 5,102,390 | 4/1992 | Crittenden et al. . |
| 5,104,376 | 4/1992 | Crittenden . |
| 5,108,416 | 4/1992 | Ryan et al. .............................. 606/194 |
| 5,324,259 | 6/1994 | Taylor et al. ............................ 604/96 |
| 5,455,646 | 10/1995 | Euteneuer et al. . |
| 5,460,608 | 10/1995 | Lodin et al. ............................. 604/96 |
| 5,571,135 | 11/1996 | Fraser et al. . |
| 5,593,412 | 1/1997 | Martinez et al. ....................... 606/108 |
| 5,603,992 | 2/1997 | Samon et al. ........................... 606/108 |
| 5,632,760 | 5/1997 | Sheiban et al. ......................... 606/191 |
| 5,690,642 | 11/1997 | Osborne et al. . |
| 5,690,644 | 11/1997 | Yurek et al. ............................ 606/108 |
| 5,772,669 | 6/1998 | Vrba ........................................ 606/108 |
| 5,776,099 | 7/1998 | Tremulis ................................. 604/96 |
| 5,807,306 | 9/1998 | Shapland et al. ....................... 604/21 |
| 5,836,965 | 11/1998 | Jendersee et al. ...................... 606/198 |

FOREIGN PATENT DOCUMENTS

| | | |
|---|---|---|
| 0 274 846 | 7/1988 | European Pat. Off. . |
| 0 442 657 | 8/1991 | European Pat. Off. . |
| 0 553 960 | 8/1993 | European Pat. Off. . |
| 0 606 165 | 7/1994 | European Pat. Off. . |
| 0 664 104 | 7/1995 | European Pat. Off. . |
| 0 707 837 | 4/1996 | European Pat. Off. . |
| 5-92043 | 4/1993 | Japan . |
| 5-161714 | 6/1993 | Japan . |
| WO93/15787 | 8/1993 | WIPO . |
| WO96/12517 | 5/1996 | WIPO . |

*Primary Examiner*—Richard J. Apley
*Assistant Examiner*—Justine R. Yu
*Attorney, Agent, or Firm*—Burns, Doane, Swecker & Mathis, LLP

[57] ABSTRACT

An stent delivery device comprises a tubular shaft body, a foldable and inflatable balloon attached to the distal end portion of the shaft body, and a stent fitted over the folded balloon. The shaft body has a lumen for inflating the balloon which communicates with the inside of the balloon. The balloon has an inflatable portion which is inflated into the shape of an approximately uniform-diameter cylinder by a fluid injected through the lumen. The stent delivery device further has a distal side stopper which is secured close to the distal end of the inflatable portion of the balloon and prevents the shift of the stent toward the distal side, and a proximal side stopper which is secured close to the proximal end of the inflatable portion of the balloon and prevents the shift of the stent toward the proximal side.

19 Claims, 13 Drawing Sheets

STENT DELIVERY DEVICE

BACKGROUND OF THE INVENTION

This invention relates to a stent delivery device used to ameliorate stenoses which form in bodily organs, such as blood vessels, bile ducts, trachea, esophagus, and urethra, especially to a stent delivery device which can implant an indwelling stent safely and easily in the intended stenosed part in blood vessels, particularly the blood vessels in the cardiovascular system in order to prevent restenosing of the treated area after the PTCA (Percutaneous Transluminal Coronary Angioplasty) treatment is performed.

The method which inserts a stent in stenosed parts of tubular organs and body cavities such as blood vessels, bile ducts, trachea, esophagus, and urethra, and thereby secures the passage space of the tubular organs and body cavities is conventionally used.

There are two types of stent used for this purpose, self-expandable stent and balloon-expandable stent, according to the function and indwelling method.

A balloon-expandable stent does not have the capability to expand by itself. This type of stent is set in an intended stenosed part by inserting a stent fitted over a balloon into the stenosed part and inflating the balloon to expand the stent (plastic deformation) and fix it in tight contact with the inside surface of that part.

A stent delivery device equipped with a balloon at the distal end is used to bring a balloon-expandable stent to an intended stenosed part, insert the stent into the stenosed part, and expand the stent in the stenosed part.

There are some conventional stent delivery devices which are provided with a stopper for preventing the stent from coming off, on the distal side of the stent expanding balloon. However, measures to prevent the stent from sliding out of place toward the proximal end are not adequate. Further, the balloons of conventional stent delivery devices have tapered portions on the distal and proximal sides of the inflatable portion which inflates into the shape of an approximately uniform-diameter cylinder. Therefore, if the stent shifts out of place on the balloon, one end portion of the stent is located over a tapered portion of the balloon. Since the tapered portions of the balloon inflate into the shape of a cone, the end portion of the stent is not fully expanded, causing an insufficient amelioration of the stenosed part.

Therefore, the object of this invention is to provide an improved stent delivery device wherein the stent fitted over the balloon rarely shifts out of position, or if the stent happens to shift a little of position, the entire stent still can be expanded completely into the desired shape.

SUMMARY OF THE INVENTION

The above object is attained by the stent delivery device of this invention which comprises a tubular shaft body, a foldable and inflatable balloon attached to the distal end portion of the shaft body, and a stent fitted over the folded balloon and expanded by the inflation of the balloon, and the shaft body having a lumen for inflating the balloon, the balloon having an inflatable portion which is inflated into the shape of an approximately uniform-diameter cylinder by the fluid injected through the lumen, and further a distal side stopper for preventing the shift of the stent toward the distal side being secured to the shaft body close to the distal end of the inflatable portion of the balloon, a proximal side stopper for preventing the shift of the stent toward the proximal side being secured to the shaft body close to the proximal end of the inflatable portion of the balloon, and a reinforcement for preventing sharp bending being secured to the outside surface of the shaft body with the distal end aligned with or near the distal end of the inflatable portion of the balloon inside the inflatable portion.

DETAILED DESCRIPTION OF THE PREFERRED EMBODIMENTS

Figure 1:
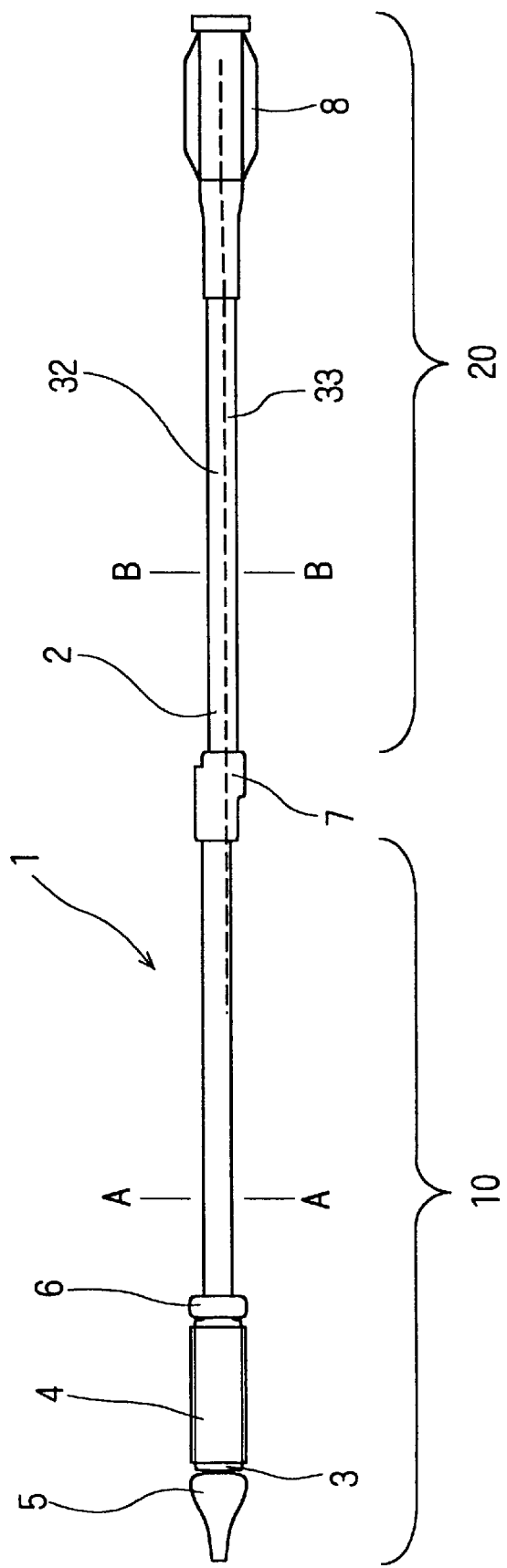
FIG. 1 is a front view of an embodiment of the stent delivery device of this invention.

The stent delivery device of this invention is described below using the embodiments shown in the drawings.

The stent delivery device of this invention 1 comprises a tubular shaft body 2, an inflatable or foldable balloon 3 attached to the distal end portion of the shaft body 2, and a stent 4 which is fit over the folded balloon 3 and expanded by inflation of the balloon 3. The shaft body 2 has a balloon inflating lumen 16 communicating with the inside of the balloon 3. The balloon 3 has an inflatable portion 31 which is inflated into a cylinder of an approximately uniform diameter by a fluid injected through the balloon inflating lumen 16. The stent delivery device 1 further comprises a distal side stopper 5 which is attached at a position close to the distal end of the inflatable portion 31 of the balloon 3 and prevents the stent 4 from shifting toward the distal end, and a proximal side stopper 6 which is attached at a position close to the proximal end of the inflatable portion 31 of the balloon 3 and prevents the stent 4 from shifting toward the proximal end side.

Next, the stent delivery device 1 embodied in a dilating device of so called rapid exchange type which has a guide wire introducing opening 36 in the middle part of the shaft body and a guide wire lumen communicating with the guide wire introducing opening 36 and being open at the distal end inside the main body is described below. This stent delivery device 1 has a guide wire lumen 15 one end of which is open at the distal end of the shaft body 2 and the other end of which is open in the middle part of the shaft body (coupler 7 described later).

This stent delivery device 1 comprises a shaft body 2, a stent-expanding balloon 3, and a stent 4 fitted over the balloon 3.

The shaft body 2 has a coupler 7 at the middle interposed between the distal side shaft portion 10 and the proximal side shaft portion 20, which have different internal structures.

Figure 2:
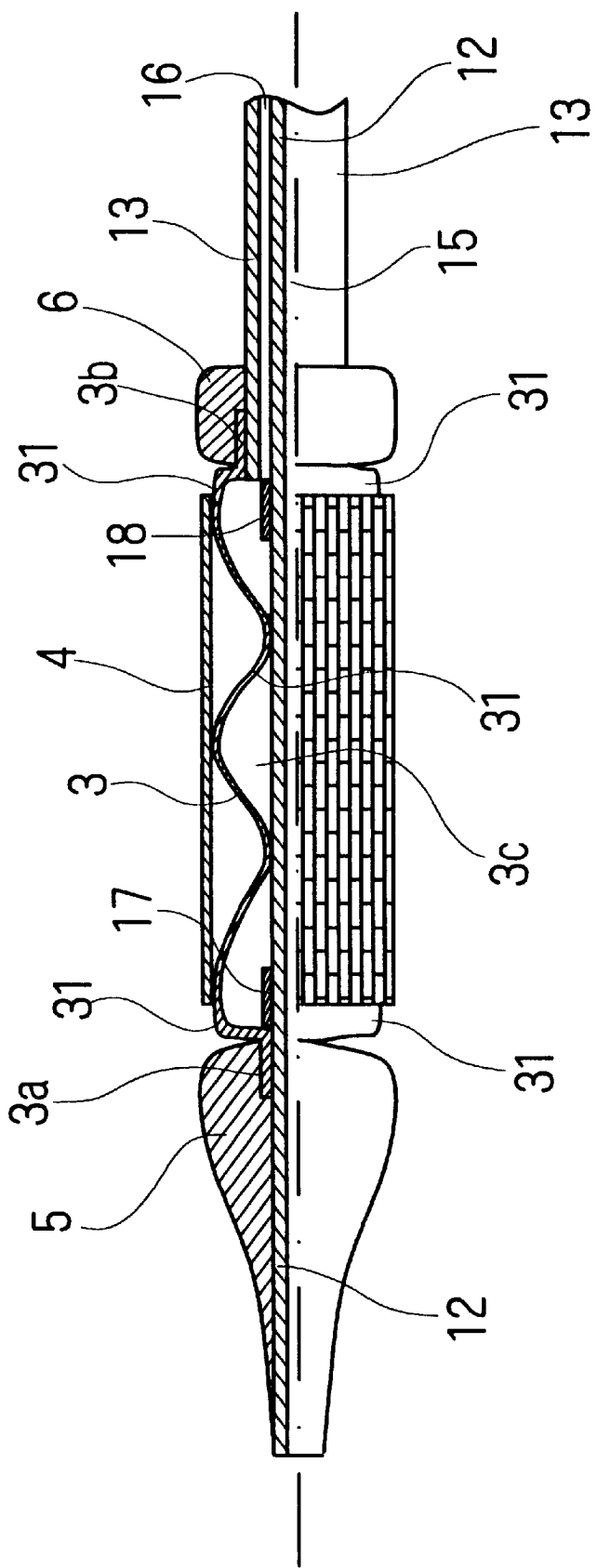
FIG. 2 is an enlarged sectional view of the distal end portion of the stent delivery device shown in FIG. 1.
Figure 3:
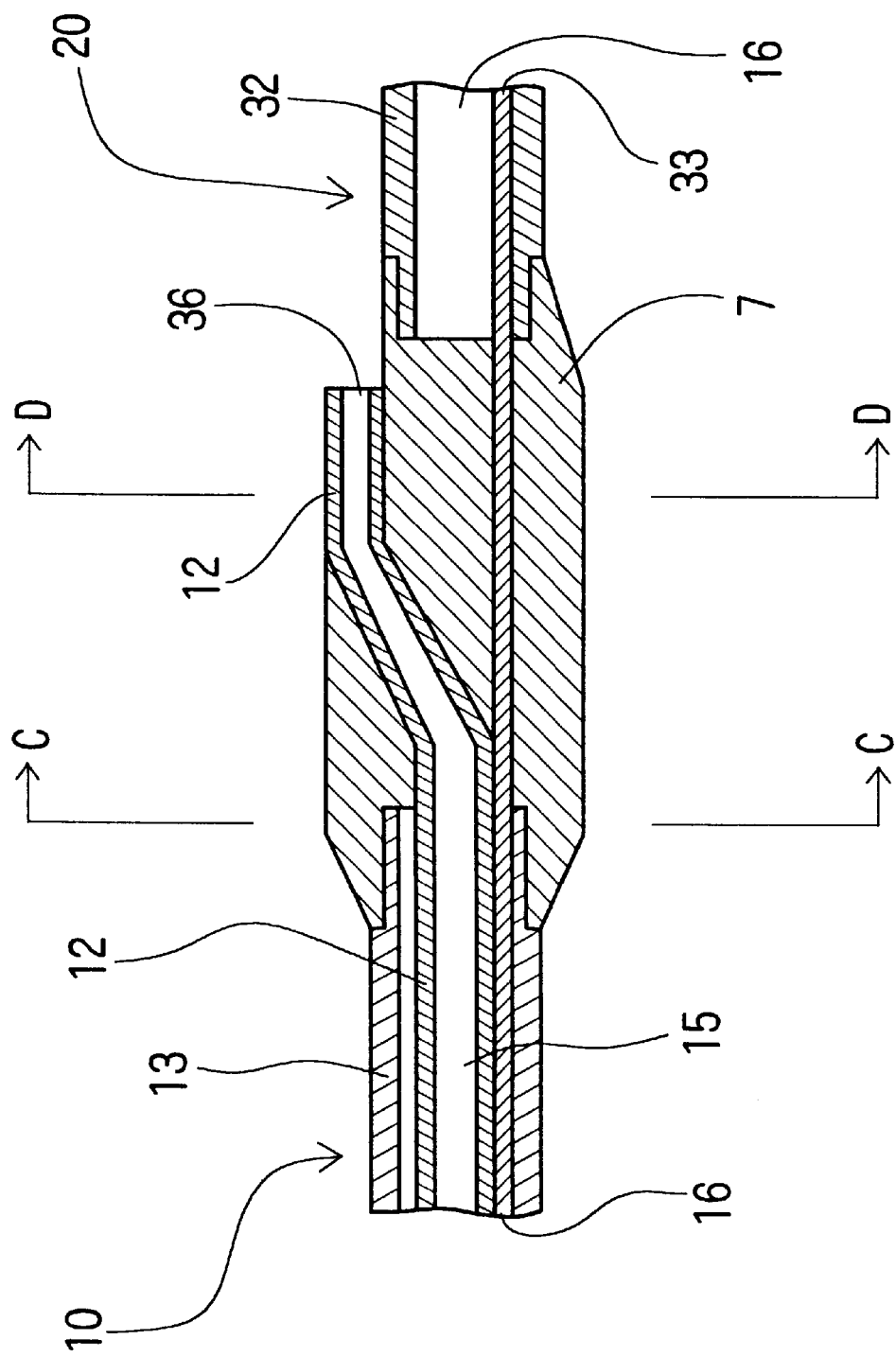
FIG. 3 is an enlarged sectional view of the joint at the middle part of the stent delivery device shown in FIG. 1.
Figure 4:
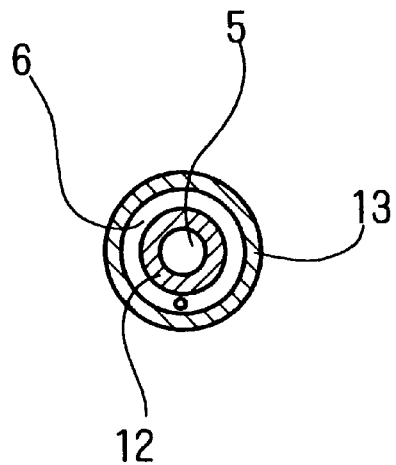
FIG. 4 is a sectional view along the A—A line of FIG. 1.

The distal side shaft portion 10 comprises an inner tube 12 which forms the guide wire lumen 15 and an outer tube 13 which encases the inner tube 12 with its distal end receded a little distance from the distal end of the inner tube 12 and forms the balloon inflating lumen 16 between the outer surface of the inner tube 12, as shown in FIGS. 2 and 3.

The balloon 3 has a distal side bonding portion 3a and a proximal side bonding portion 3b. The distal side bonding portion 3a is bonded to the inner tube at a position a little distance proximal from the distal end of the inner tube 12, and the proximal side bonding portion 3b to the distal end portion of the outer tube 13.

The balloon 3 communicates with the balloon inflating lumen 16 near its proximal end.

The distal side stopper 5 is attached to the distal end portion of the inner tube 12 so as to cover the distal end portion of the distal side bonding portion 3a of the balloon 3. That entire the distal side bonding portion 3a of the balloon 3 is covered with the distal side stopper 5 is desirable. The distal side stopper 5 is formed of an elastic material in a ring with the exterior diameter of the proximal end portion approximately equal to or a little larger than that of the stent 4.

The distal side stopper 5 is tapered so as to become gradually smaller in exterior diameter toward the distal end. By forming the distal side stopper 5 in this shape, the distal side stopper 5 has the function of leading the dilating device to the intended stenosed part. As a result, insertion of the stent-holding portion of the dilating device into a stenosed part of a body organ (blood vessels, for example) is made easy.

The stopper 5 may be divided into a stopper portion without taper and a tapered portion which becomes gradually smaller in diameter toward the distal end of the shaft body between the stopper portion and the distal end of the shaft body.

Figure 5:
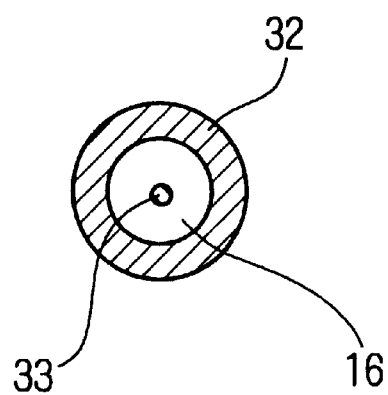
FIG. 5 is a sectional view along the B—B line of FIG. 1.

The proximal side stopper 6 formed of an elastic material is attached to the distal end portion of the outer tube 13 so as to cover the proximal end portion of the proximal side bonding portion 3b of the balloon 3. That entire the proximal side bonding portion 3b of the balloon 3 is covered with the proximal side stopper 6 is desirable. The proximal side stopper 6 also has an exterior diameter (at the distal end portion) approximately equal to or a little larger than that of the stent 4. Similarly to the distal side stopper 5, the proximal side stopper 6 may be tapered to become gradually smaller in exterior diameter toward the proximal side (in the direction away from the balloon 3) as shown in FIG. 5. The stopper 6 may also be divided into a stopper portion without taper and a tapered portion which becomes gradually smaller in diameter toward the proximal end of the shaft body.

The above-described stoppers each cover the corresponding bonding portions (at least their end portions) of the balloon 3. This prevents the end of each bonding portion of the balloon 3 from being exposed, and further increases the strength of bonding.

The stent 4 described later is put between the two stoppers and prevented form moving beyond the stoppers. Further, the distal end of the stent 4 is very close to the distal side stopper 5, and the proximal end of the stent 4 is close to the proximal side stopper 6. As the result, the edge of both ends of the stent 4 does not come into contact with the inside surface of bodily organs (inside surface of blood vessels, for example), being prevented from inflicting injuries on the inside wall of body organs.

The inner tube 12 is within the range of 0.35 to 1.0 mm, preferably 0.45 to 0.8 mm in exterior diameter and within the range of 0.2 to 0.9 mm, preferably 0.35 to 0.7 mm in interior diameter. The outer tube 13 is within the range of 0.6 to 1.5 mm, preferably 0.8 to 1.1 mm in exterior diameter and within the range of 0.5 to 1.4 mm, preferably 0.7 to 1.0 mm in interior diameter.

For the material for forming the inner tube 12, outer tube 13, and stoppers 5 and 6, substances with an appropriate elasticity including thermoplastic resins [polyolefin (polyethylene, polypropylene, ethylene-propylene copolymer, ethylene-vinyl acetate copolymer, and their fully or partly cross-linked form, etc.), poly(vinyl chloride), polyamide elastomer, polyurethane, etc.], silicone rubber, and Latex rubber, for example, are usable. The above-described thermoplastic resins are preferable, and the fully cross-linked or partly cross-linked above-described polyolefin are more preferable. For the material for the distal side stopper 5, substances with bondability to the material of the inner tube 12 are used. For the material of the proximal side stopper 6, substances with bondability to the material of the outer tube 13 are used.

The balloon 3 is foldable, and folded so as to fit over the outside surface of the inner tube 12 when it is not inflated. The balloon 3 has an inflatable portion 31 which is inflated into the shape of a cylinder (preferably circular cylinder) with an approximately uniform exterior diameter and thereby expands the stent 4. The shape of inflated inflatable portion 31 need not be a circular cylinder, and may be a polygonal cylinder, for example. The balloon 3 has a distal side bonding portion 3a and a proximal side bonding portion 3b for attaching it to the shaft body 2 so that it can be inflated by a fluid injected through the balloon inflating lumen 16. The distal side bonding portion 3a and the proximal side bonding are bonded to the inner tube 12 and the outer tube 13, respectively, by an adhesive or welding in the liquid-tight fashion. The balloon 3 is a taper-less balloon which practically does not have a tapered portion (taper inflatable portion) formed between the inflatable portion 31 and each of bonding portions 3a and 3b. Therefore, the distal side stopper 5 is disposed on the shaft body 2 (inner tube 12, to be exact) close to the distal end of the inflatable portion 31 of the balloon 3. Similarly, the proximal side stopper 6 is disposed on the shaft body 2 (outer tube 13, to be exact) close to the proximal end of the inflatable portion 31 of the balloon 3.

The balloon 3 forms an inflating space 3c between its inside surface and the outside surface of the inner tube 12 as shown in FIG. 2. The inflating space 3c communicates with the lumen 16 on entire circumference at the proximal end region. Since the space 3c thus communicates with the balloon inflating lumen 16 having a comparatively large sectional area, injection of an inflating fluid into the balloon 3 through the lumen 16 is made easy.

For the material for the balloon 3, substances with an appropriate elasticity, including thermoplastic resins [polyolefin (polyethylene, polypropylene, ethylene-propylene copolymer, ethylene-vinyl acetate copolymer, and cross-linked ethylene-vinyl acetate copolymer, etc.), poly (vinyl chloride), polyamide elastomer, polyurethane, polyester (polyethylene terephthalate, etc.), and polyarylene sulfide (polyphenylene sulfide, etc.)], silicone rubber, and Latex rubber, for example, are usable. Orientable or drawable materials are particularly preferable. The balloon 3 is preferably oriented in the directions of two axes so that it has a high strength and a high expansive power.

The balloon 3 has the following size. The cylindrical portion (inflated inflatable portion 31) is within the range of 2.0 to 4.0 mm, preferably 2.5 to 3.5 mm in exterior diameter, and within the range of 10 to 50, preferably 20 to 40 mm in length. The distal side bonding portion 3a is within the range of 0.9 to 1.5 mm, preferably 1.0 to 1.3 mm in exterior diameter, and within the range of 1.0 to 5.0 mm, preferably 1.0 to 1.3 mm in length. The proximal side bonding portion 3b is within the range of 1.0 to 1.6 mm, preferably 1.1 to 1.5 mm in exterior diameter, and within the range of 1.0 to 5.0 mm, preferably 2.0 to 4.0 in length.

A distal side reinforcement 17 is attached to the outside surface of the shaft body 2 (inner tube 12 in this embodiment) at a position which is close to the distal side stopper 5 and also close or contacting to the distal end of the inflatable portion 31 of the balloon 3 inside the inflatable portion 31. Similarly, a proximal side reinforcement 18 is attached to the outside surface of the shaft body 2 (inner tube 13 in this embodiment) at a position which is close to the proximal side stopper 6 and also close or contacting to the proximal end of the inflatable portion 31 inside the inflatable portion 31. By adding such reinforcements, the shaft body 1 can be prevented from kinking between each stopper and the stent 4.

Figure 14:
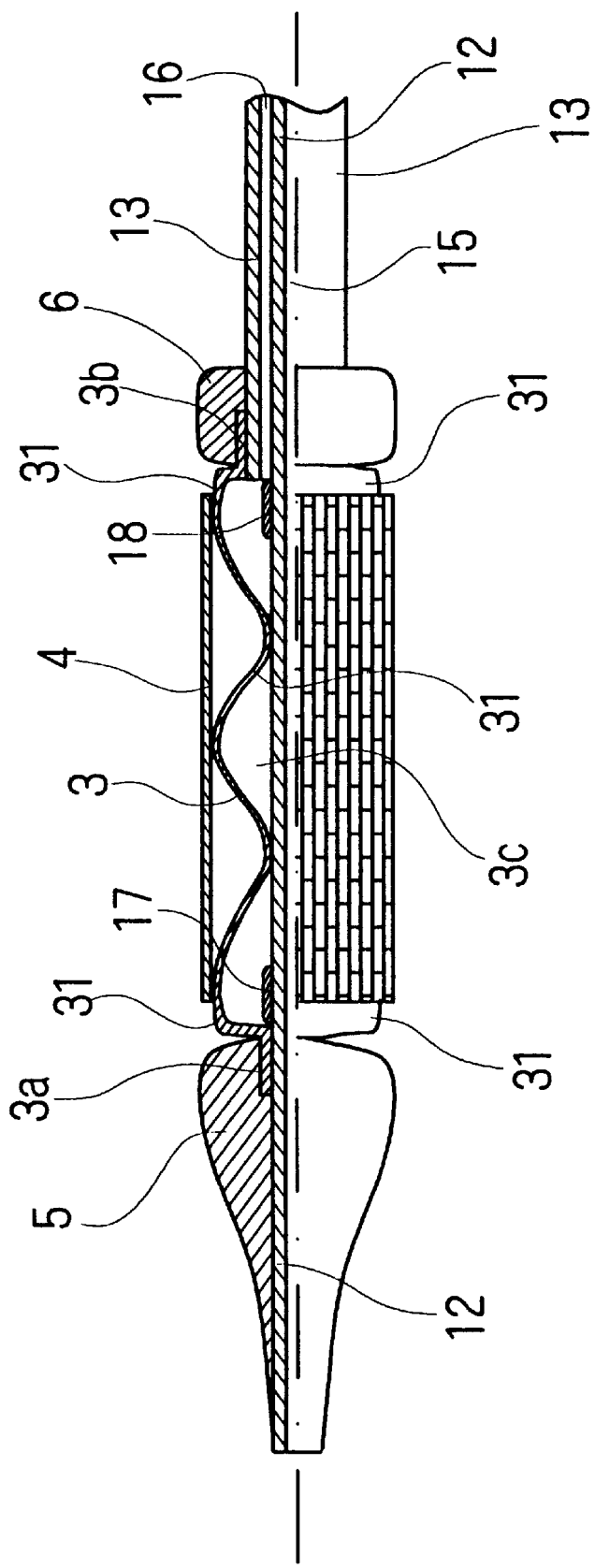
FIG. 14 is an enlarged sectional view of the distal end portion of another embodiment of the stent delivery device of this invention.

The distal end of the distal side reinforcement 17 is preferably located to the distal side of the distal end of the stent 4. The proximal end of the proximal side reinforcement 18 is preferably located to the proximal side of the proximal end of the stent 4. The proximal portion of the distal side reinforcement 17 is preferably located inside the stent 4. The distal end portion of the proximal side reinforcement 18 is preferably located inside the stent 4. The outer edge of the distal end of the distal side reinforcement 17 is preferably rounded, as shown in FIG. 14. The outer edges of the distal and proximal ends of the distal side reinforcement 17 is more preferably rounded, as shown in FIG. 14. The outer edges of the distal and proximal ends of the proximal side reinforcement 18 is preferably rounded, as shown in FIG. 14.

In this embodiment, the distal side reinforcement 17 is disposed inside the inflatable portion 31 of the balloon 3 with the distal end aligned with the distal end of the inflatable portion 31. The proximal side reinforcement 18 is disposed inside the inflatable portion 31 of the balloon 3 with the proximal end approximately aligned with the proximal end of the inflatable portion 31. However, the reinforcements 17 and 18 may be disposed at a position a little distance inward to the middle of the inflatable portion 31.

The reinforcements 17 and 18 may also be disposed so that they are partly covered by the corresponding bonding portions of the balloon 3. Further, the reinforcements 17 and 18 may be disposed so that they are partly covered by the corresponding bonding portions of the balloon 3 and the corresponding stoppers. The position of the distal end of the distal side reinforcement 17 is preferably within 3 mm on both sides from the distal end of the inflatable portion 31 of the balloon 3.

Figure 15:
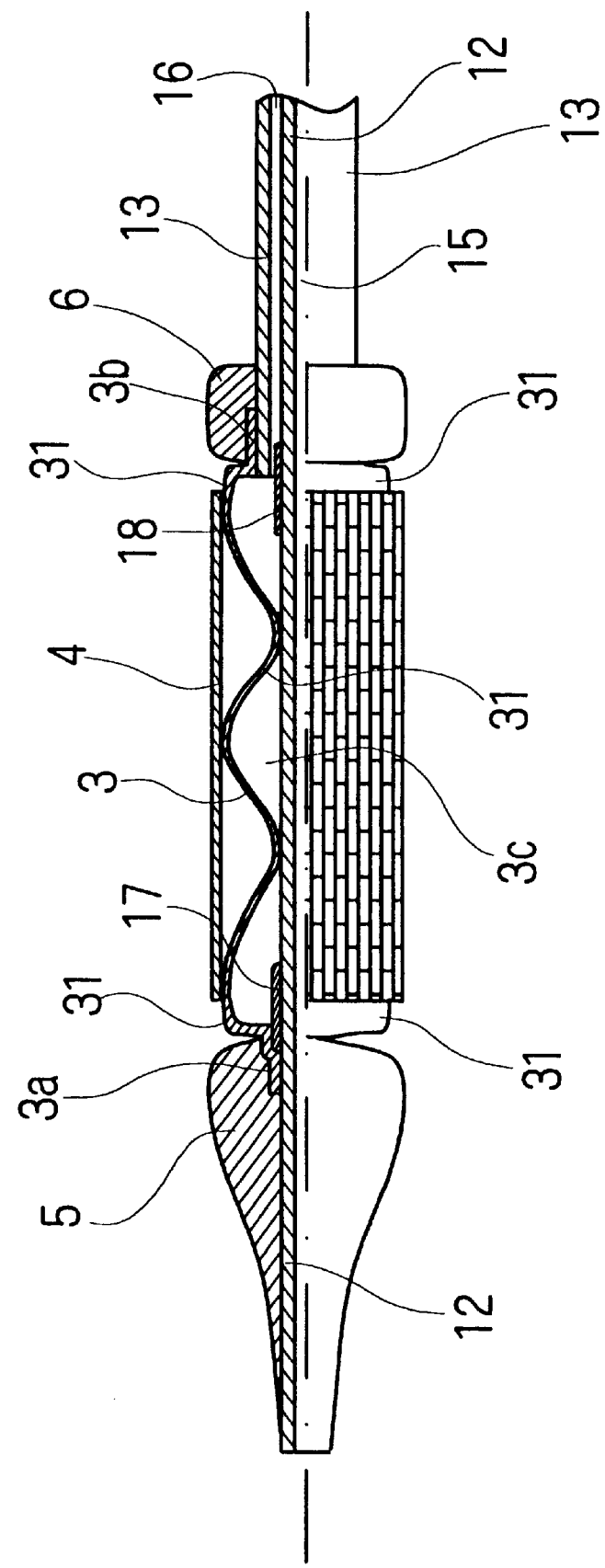
FIG. 15 is an enlarged sectional view of the distal end portion of another embodiment of the stent delivery device of this invention.

A distal portion of the reinforcement 17 may be disposed so as to be covered by the distal bonding portion 3a of the balloon 3, as shown in FIG. 15. Further, the distal bonding portion 3a of the balloon 3 covering with the distal portion of the reinforcement 17 may be covered by the distal side stopper 5, as shown in FIG. 15.

A proximal portion of the proximal side reinforcement 18 may be located inside the distal end portion of the outer tube 13, as shown in FIG. 15. The proximal portion of the proximal side reinforcement 18 shown in FIG. 15 overlaps to the distal end portion of the proximal side stopper 6.

The reinforcements 17 and 18 may be in the shape of a ring of a predetermined length or a wound coil of wire. The reinforcements is preferably made of an X-ray opaque material (gold, platinum, tungsten or an alloy of them, or silver-palladium, for example). By using an X-ray opaque material, the position of the distal side and proximal ends of the inflatable portion 31 of the balloon 3, and hence the positions of the distal side and proximal ends of the stent 4 can be known from the X-ray shadow of the reinforcements.

The stent 4 implanted by the stent delivery device 1 of this invention has the form of practically a cylinder with an exterior diameter suited to insertion into the intended bodily organ. It can be expanded by the force in the outward radial direction when the balloon 3 inflates, as called a balloon-expandable stent.

Figure 9:
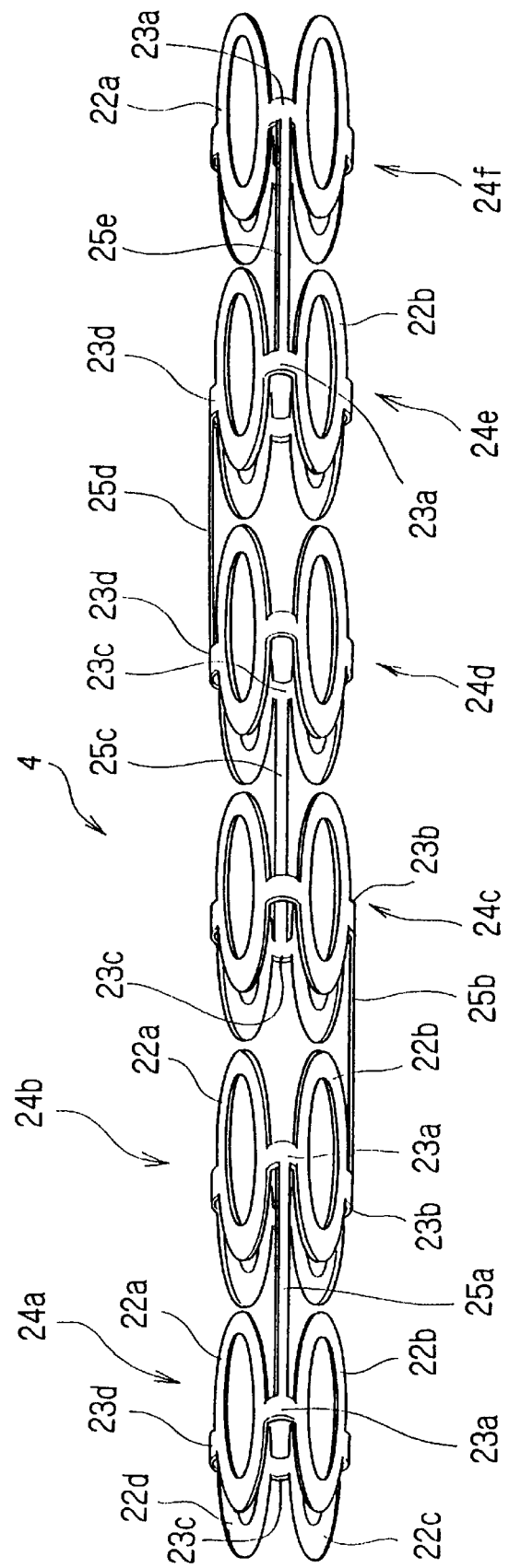
FIG. 9 is a perspective view of an example of the stent that is used along with the stent delivery device of this invention.

The stent 4 has the structure as shown in FIG. 9, for example. Elliptical or polygonal ring-like elements 22, longer in the direction of the axis of the stent 4 than in the circumferential direction and having a vacant center, are arranged around the center axis of the stent 4 on a circumference at equal angular intervals, adjacent elements are connected by a connecting portion 23 (23a, 23b, 23c, and 24d) whose ends connects with the portions of the adjacent elements opposite to each other to form a ring unit 24 (24a, 24b, 24c, 24d, 24e, and 24f). A plurality of the ring units 24a, 24b, 24d, 24e, and 24f are arranged coaxially on the axis of the stent 4, and adjacent ring units 24 are connected by at least a connecting portion 25 (25a, 25b, 25c, 25d, and 25e) each end of which connects with a connecting portion 23 of each of the adjacent ring units 24. The form of the stent 4 is not limited to this one, and may also be a network or other known ones.

For the material for the stent 4, substances with an appropriate biocompatibility, such as a stainless steel, tantalum and an alloy of tantalum, platinum and an alloy of platinum, gold and an alloy of gold, and a cobalt-based alloy, are preferable. The stent 4 may be coated with plating of a precious metal (gold or plutonium) after the stent 4 is formed. Of stainless steels, SUS316L with the highest corrosion resistance is preferable.

It is preferable to anneal the stent after the stent is formed into the final shape. By annealing the stent, the flexibility and plasticity of the entire stent increase, and hence the stent's abidability at an indwelled position of a winding blood vessel improves. Further, the force of tending to return to the original shape after the stent is inflated, especially the force of tending to return to the straight which occurs when the stent is expanded at a bending portion of a blood vessel decreases in comparison with that of the stent not annealed. As the result, the physical stimuli exerted on the inside surface of bent portions of blood vessels decrease, and the causes of restenosis are eliminated. Annealing is preferably performed by heating the stent to 900 to 1200° C. in an inert gas (argon gas, for example) and then cooling it slowly so that oxide film does not form on the surface of the stent.

The diameter of the stent 4 when it is not expanded is preferably within the range of approximately 0.9 to 1.5 mm, and more preferably within the range of 1.0 to 1.3 mm. The length of each ring unit, or the length of each element in the axial direction is preferably within the range of approximately 1.5 to 4.0 mm, and especially within the range of 2.0 to 3.0 mm. The number of the ring units is preferably within the range of 3 to 10. The wall thickness of the ring units at both ends is preferably within the range of approximately 0.05 to 0.07 mm. The wall thickness of the ring units in the middle portion is preferably within the range of approximately 0.05 to 0.12, and preferably within the range of 0.06 to 0.10 mm. The wall thickness of the ring units at both ends is preferably ⅗ to ⅘ of that of the ring units in the middle portion.

Next, the proximal side shaft portion 20 of the shaft body 2 is described with reference to FIGS. 5 to 8.

The proximal side shaft portion 20 comprises a shaft tube 32 and a hub connected to the proximal end of the shaft tube 32. A rigidity-imparting member 33 is inserted in the shaft tube 32. The proximal end of the rigidity-imparting member 33 is secured to the shaft tube 32, and the distal end extends from the distal end of the shaft tube 32 into the distal side shaft portion 10 through the coupler 7. In this embodiment, the distal end of the rigidity-imparting member 33 extends to between the inner tube 12 and the outer tube 13 of the distal side shaft portion, or in the balloon inflating lumen 16.

The rigidity-imparting member 33 extends from the proximal end of the shaft tube 32 toward the distal end inside the shaft tube 32. Not to prevent the shaft body 2 bending, the rigidity-imparting member 33 is secured to the shaft tube 32 or the hub 8 only at the proximal end portion, and the other portion of the rigidity-imparting member 33, specifically the portion inside the shaft tube 32 except the proximal end portion, the coupler 7, and the distal side shaft portion (between the inner tube 12 and the outer tube 13) is not secured.

The rigidity-imparting member 33 prevents too sharp bending of the shaft tube 32 at bent portions of blood vessels and meandering of the shaft tube 32 within a blood vessel, without excessively decreasing the flexibility of the shaft tube 32. The rigidity-imparting member 33 is preferably formed of a wire. For the wire, metal wire of an elastic metal (a stainless steel, etc.) or a super elastic alloy within the range of 0.05 to 1.5 mm, preferably 0.1 to 1.0 mm in diameter is preferable. Wire of a high tensile strength stainless steel for spring or a super elastic alloy is particularly preferable.

A super elastic alloy here refers to an alloy which is generally called a shape-memory alloy and exhibits a super elasticity at least at the body temperature (around 37° C.). Preferable super elastic alloys are Ti-Ni alloy with 49 to 53 atom percent of Ni, Cu-Zn alloy with 38.5 to 41.5 wt % of Zn, Cu-Zn-X alloy with 1 to 10 wt % of X (X=Be, Si, Sn, Al, or Ga), and Ni-Al alloy with 36 to 38 atom percent of Al. The Ti-Ni alloy above is particularly preferable. The mechanical property of the Ti-Ni alloy above can be altered as desired by replacing period of the Ti-Ni alloy with 0.01 to 10.0 atom percent of X to form Ti-Ni-X alloy (X=Co, Fe, Mn, Cr, V, Al, Nb, W, B, etc.), replacing part of the Ti-Ni alloy with 0.01 to 30.0 atom percent of X to form Ti-Ni-X alloy (X=Cu, Pd, or Zr), or selecting the reduction ratio of cold working and/or the conditions of the final heat treatment. The mechanical property of the Ti-Ni-X alloy above can be altered as desired by selecting the reduction ratio of cold working and/or the conditions of the final heat treatment.

The shaft tube 32 has the hub 8 attached to the proximal end portion. The proximal end portion of the rigidity-imparting member 33 is secured to the proximal end portion of the shaft tube 32. The shaft tube 32 has a balloon inflating fluid injecting opening 34 formed at a position a little distance distal from the proximal end. A kink preventing tube 35 is attached to the outside surface of the portion around the boundary between the hub 8 and the shaft tube 32 (or around the distal end of the hub 8) so as to cover that portion. The connector for connecting the balloon inflating fluid injecting device is formed in the proximal end of the hub 8.

The shaft tube 32 is within the range of 0.6 to 1.5 mm, preferably 0.8 to 1.3 mm in exterior diameter, and within the range of 0.5 to 1.4 mm, preferably 0.7 to 1.2 mm in interior diameter.

For the material for forming the shaft tube 32, substances with an appropriate elasticity including thermoplastic resins [polyolefin polyethylene, polypropylene, ethylene-propylene copolymer, ethylene-vinyl acetate copolymer, etc.), poly(vinyl chloride), polyamide elastomer, polyimide, polyurethane, etc.], silicone rubber, and Latex rubber, for example, are usable. Thermoplastic resins are preferable.

For the material for forming the distal side stopper 5, a substance with a bondability to the material for the inner tube 12 is used. For the material for forming the proximal side stopper 6, a substance with a bondability to the material for the outer tube 13 is used.

Figure 6:
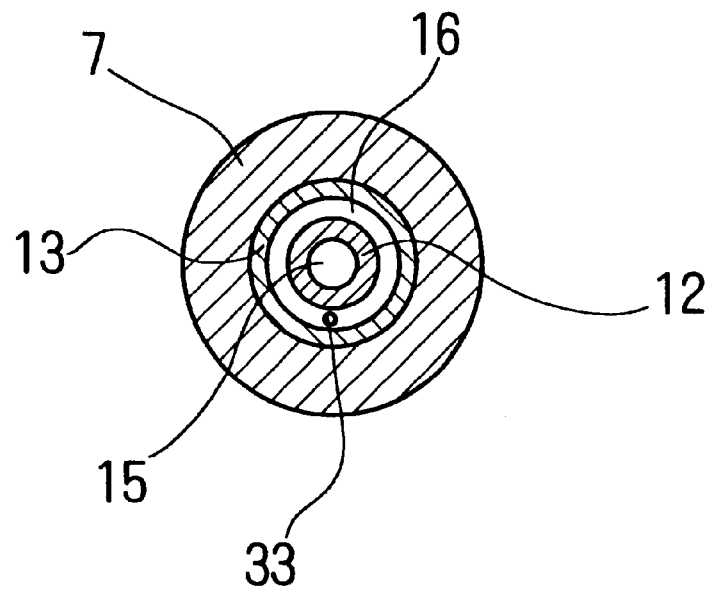
FIG. 6 is a sectional view along the C—C line of FIG. 3.
Figure 7:
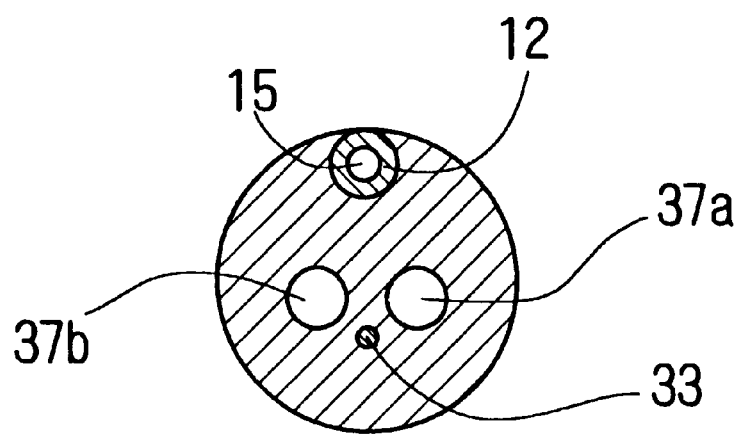
FIG. 7 is a sectional view along the D—D line of FIG. 3.
Figure 8:
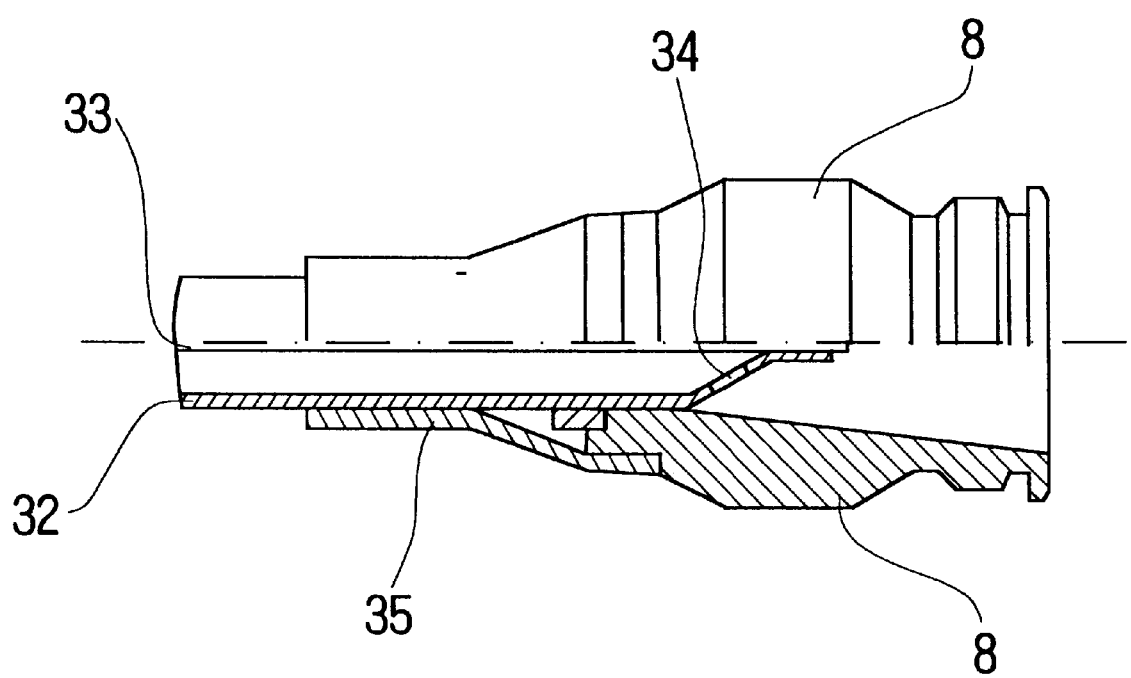
FIG. 8 is an enlarged sectional view of the proximal end portion of the stent delivery device shown in FIG. 1.

The distal side shaft portion 10 and the proximal side shaft portion 20 are joined together by the coupler 7. The coupler 7 has a hole for inserting the inner tube 12 which extends coaxially from the distal end to the middle part, bends at the middle part, and extends obliquely to the axis to open in the outside circumferential surface of the proximal end portion as shown in FIGS. 3, 6, and 7. The proximal end portion of the inner tube 12 is passed through the hole for inserting the inner tube and extends from the opening in the circumferential surface of the coupler 7. The proximal end of the protruded portion of the inner tube 12 serves as the guide wire introducing opening 36. The coupler 7 also has balloon inflating fluid passages 37a and 37b extending from the distal end to the proximal end formed. In this example, two balloon inflating fluid passages are formed as shown in FIG. 7. The balloon inflating lumen formed between the inner tube 12 and the outer tube 13 and the balloon inflating lumen 16 inside the shaft tube 32 are communicated with each other by these balloon inflating fluid passages. Further, the coupler 7 has a rigidity-imparting member passage hole which extends from the distal end to the proximal end. The rigidity-imparting member is passed through the hole.

Figure 11:
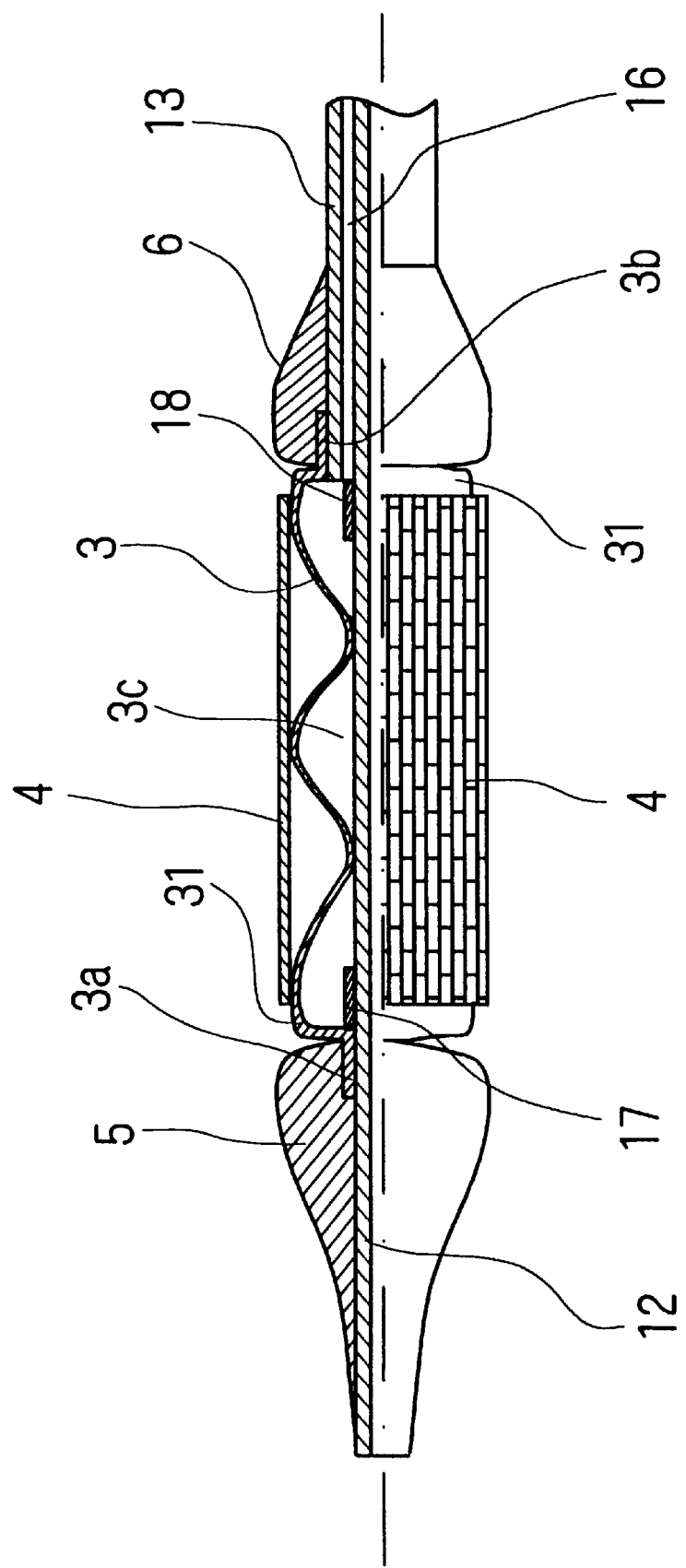
FIG. 11 is an enlarged sectional view of the distal end portion of the stent delivery device shown in FIG. 10.
Figure 12:
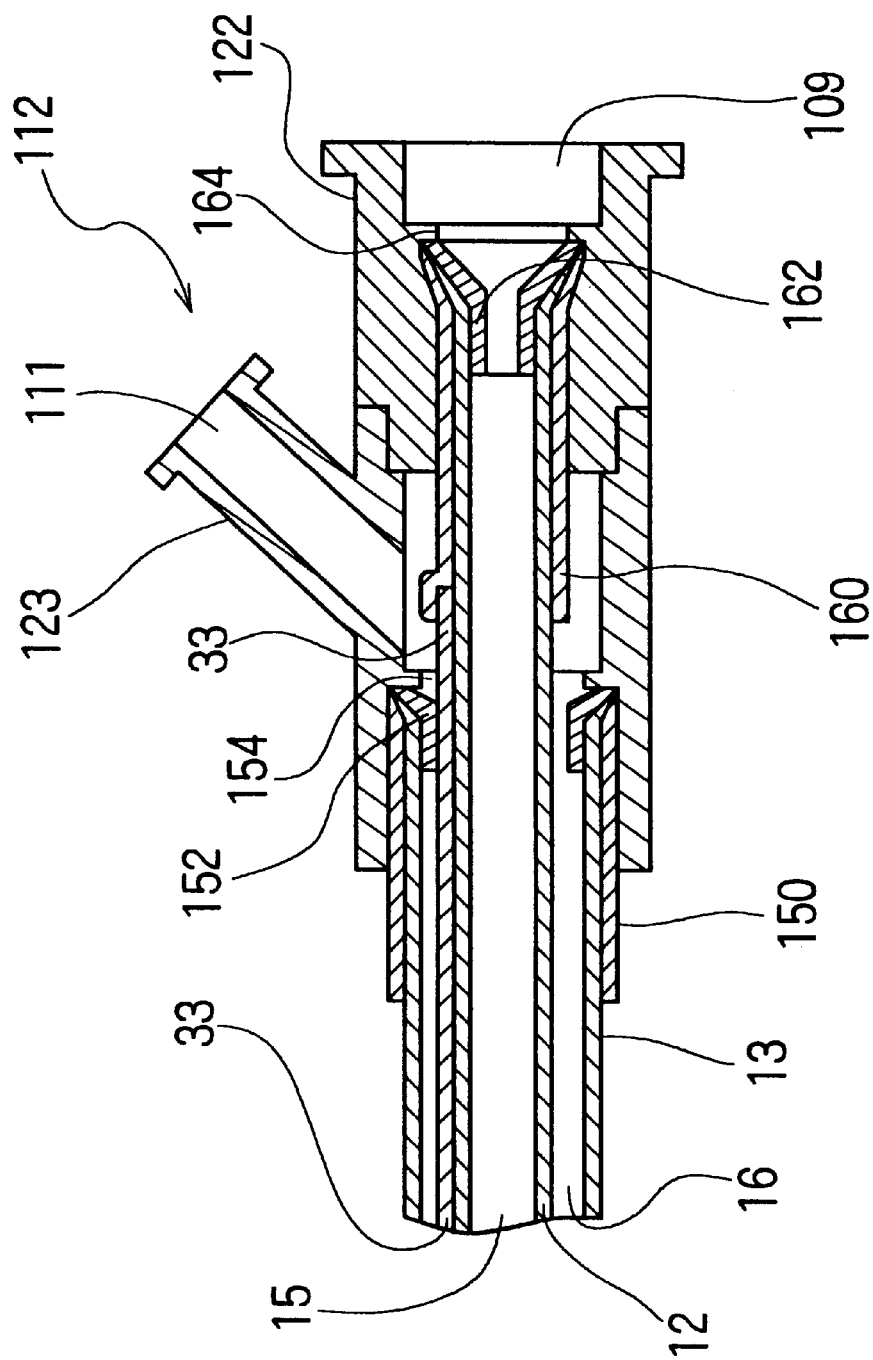
FIG. 12 is an enlarged sectional view of the proximal end portion of the stent delivery device shown in FIG. 10.

Next, the stent delivery device of another embodiment of this invention is described with reference to FIGS. 10 to 12.

Figure 10:
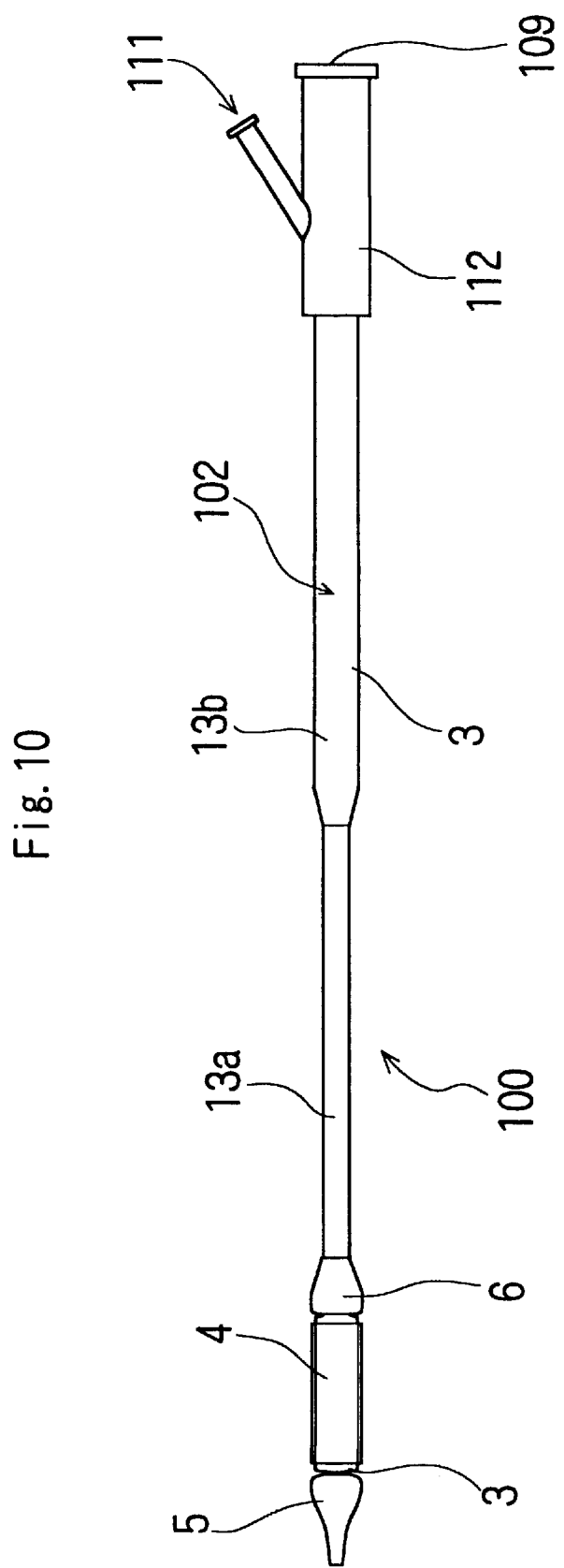
FIG. 10 is a front view of another embodiment of the stent delivery device of this invention.

FIG. 10 is a front view of the stent delivery device of another embodiment of this invention. FIG. 11 is an enlarged sectional view of the distal end portion of the stent delivery device shown in FIG. 10. FIG. 12 is an enlarged sectional view of the proximal end portion of the stent delivery device shown in FIG. 10.

In the stent delivery device 100 of this embodiment, the shaft body 102 has a guide wire lumen 15 one end of which is open at the distal end of the shaft body 102 and the other end of which is open at the proximal end of the shaft body.

The difference between the stent delivery device 100 of this embodiment and the stent delivery device 1 described above and shown in FIGS. 1 to 7 is only in the structure of the shaft body 102 and the shape of the proximal side stopper 6. The other parts of the stent delivery device 1 and 100 are the same.

This stent delivery device 100 comprises a shaft body 102, a stent expanding balloon 3 attached to the distal end portion of the shaft body 102, and a stent 4 held over the balloon 3. The shaft body 102 comprises an inner tube 12, an outer tube 13 and a hub 112.

The inner tube 12 is a tube which has a guide wire lumen 15 within it for inserting the guide wire. The inner tube 12 is within the range of 100 to 2000 mm in length, preferably 150 to 1500 mm, within the range of 0.1 to 1.0 mm, preferably 0.3 to 0.7 mm in exterior diameter, and within the range of 10 to 150 μm, preferably 20 to 100 μm in wall thickness. The inner tube 12 is held within the outer tube 13, and its distal end portion extends from the outer tube 13. A balloon inflating lumen 16 is formed by the outside surface of the inner tube 12 and the inside surface of the outer tube 13, and it has an adequate cross-sectional area. The outer tube 13 is a tube which encases the inner tube 12 with the distal end receded a little distance from the distal end of the inner tube 12.

The outer tube 13 is within the range of 100 to 2000 mm, preferably 150 to 1500 mm in length, within the range of 0.5 to 1.5 mm, preferably 0.7 to 1.1 mm in exterior diameter, and within the range of 25 to 200 μm, preferably 50 to 100 μm in wall thickness.

In the stent delivery device 100 of this embodiment, the outer tube 13 consists of a distal side outer tube 13a and a main outer tube 13b joined together. The distal side outer tube 13a tapers toward the distal end in the portion near the joint to the main outer tube 13b, and the portion from the tapered portion to the distal end is smaller in exterior diameter.

The exterior diameter of the small-diameter portion of the distal side outer tube 13a is within the range of 0.50 to 1.5 mm, preferably 0.60 to 1.1 mm. The exterior diameter of the proximal end portion of the distal side outer tube 13a and that of the main outer tube 13b is within the range of 0.75 to 1.5 mm, preferably 0.9 to 1.1 mm.

The balloon 3 has a distal side bonding portion 3a and a proximal side bonding portion 3b. The distal side bonding portion 3a is bonded to the inner tube 12 at a position a little distance proximal from the distal end of the inner tube 12, and the proximal side bonding portion 3b to the distal end portion of the outer tube. The balloon 3 communicates with the balloon inflating lumen 16 near its proximal end.

A distal side stopper 5 is attached to the distal end portion of the inner tube 12 so as to cover the distal end portion of the distal side bonding portion 3a of the balloon 3. That entire the distal side bonding portion 3a of the balloon 3 is covered with the distal side stopper 5 is desirable. The distal side stopper 5 is formed of an elastic material in a ring-like shape. The exterior diameter of the proximal end of the stopper 5 is approximately equal to or a little greater than the exterior diameter of the stent 4. The distal side stopper 5 is tapered so as to become gradually smaller in diameter toward the distal end. By forming the distal side stopper 5 in this shape, the distal side stopper 5 can be endowed with the function of leading the dilating device to the stenosed part to treat, and the insertion of the stent-bringing portion of the dilating device into a stenosed part of a body organ is made easy.

The proximal side stopper 6, made of an elastic material, is attached to the distal end portion of the outer tube 13 so as to cover the proximal end portion of the proximal side bonding portion 3b of the balloon 3. That entire the proximal side bonding portion 3b of the balloon 3 is covered with the proximal side stopper 6 is desirable. The exterior diameter of the proximal side stopper 6 is approximately equal to or a little greater than that of the stent 4. Similarly to the distal side stopper 5, the proximal side stopper 6 may also be tapered so as to become gradually smaller in diameter toward the proximal end (in the direction away from the balloon 3). By forming the stent delivery device in this shape, pulling the stent delivery device out of a bodily organ or the guide catheter becomes easier.

The distal side stopper may be divided into a stopper portion without taper and a tapered portion which becomes gradually smaller in diameter toward the distal end of the shaft body. Similarly, the proximal side stopper may be divided into a stopper portion without taper and a tapered portion which becomes gradually smaller in diameter toward the proximal end of the shaft body.

The stent 4 is retained between these two stoppers. The distal end of the stent 4 is close to the distal side stopper 5, and the proximal end of the stent 4 to the proximal side stopper 6.

For the materials for forming the inner tube 12, outer tube 13, and stopper, substances with an appropriate elasticity.

For the material for forming the inner tube 12, outer tube 13, and stoppers 5 and 6, substances with an appropriate elasticity including thermoplastic resins [polyolefin (polyethylene, polypropylene, ethylene-propylene copolymer, ethylene-vinyl acetate copolymer, etc.), poly (vinyl chloride), polyamide elastomer, polyurethane, etc.], silicone rubber, and Latex rubber, for example, are usable. The above-described thermoplastic resins are preferable, and the above-described polyolefin are particularly preferable. For the material for forming the distal side stopper 5, a substance with a bondability to the material for the inner tube 12 is used. For the material for forming the proximal side stopper 6, a substance with a bondability to the material for the outer tube 13 is used.

The balloon 3 is foldable, and folded so as to fit over the outside surface of the inner tube 12 when it is not inflated. The balloon 3 has an inflatable portion 31 in the shape of a cylinder (preferably circular cylinder) with an approximately uniform exterior diameter for expanding the stent 4. The shape of the inflatable portion 3 need not be a circular cylinder, and may be a polygonal cylinder. The distal side bonding portion 3a is bonded to the inner tube 12 and the outer tube 13 to the distal end portion of the outer tube 13, by an adhesive or welding in the liquid-tight fashion. The balloon 3 is a taper-less balloon which practically does not have a tapered portion formed between the inflatable portion 31 and each of bonding portions 3a and 3b. Therefore, the distal side stopper 5 is disposed on the shaft body 102 (inner tube 12, to be exact) close to the distal end of the inflatable portion 31 of the balloon 3. Similarly, the proximal side stopper 6 is disposed on the shaft body 102 (outer tube 13, to be exact) close to the proximal end of the inflatable portion 31 of the balloon 3.

The balloon 3 forms an expanding space 3c between its inside surface and the outside surface of the inner tube 12. The expanding space 3c communicates with the balloon expanding lumen 16 on entire circumference at its proximal end portion. Since the space 3c thus communicates with the balloon inflating lumen 16 having a comparatively large cross-sectional area, injection of a fluid into the balloon 3 through the lumen 16 is made easy.

The size and material of the balloon 3 is the same as those described above.

A distal side reinforcement 17 is attached to the outside surface of the shaft body 102 (inner tube 12 in this embodiment) at a position which is close or contacting to the distal side stopper 5 and also close to the distal end of the inflatable portion 31 of the balloon 3 inside the inflatable portion 31. Similarly, a proximal side reinforcement 18 is attached to the outside surface of the shaft body 102 (outer tube 13 in this embodiment) at a position which is close or contacting to the proximal side stopper 6 and also close to the proximal end of the inflatable portion 31 inside the inflatable portion. By adding such reinforcements, kinking of the shaft body 102 between each stopper and the stent 4 can be prevented.

The distal end of the distal side reinforcement 17 is preferably located on the distal side of the distal end of the above-described stent 4. The proximal end of the proximal side reinforcement 18 is preferably located on the proximal side of the proximal end of the stent 4. The proximal portion of the distal side reinforcement 17 is preferably located inside the stent 4. The distal end portion of the proximal side reinforcement 18 is preferably located inside the stent 4. The outer edge of the distal end of the distal side reinforcement 17 is preferably rounded. The outer edges of the distal and proximal ends of the distal side reinforcement 17 is more preferably rounded. The outer edges of the distal and proximal ends of the proximal side reinforcement 18 is preferably rounded.

In this embodiment, the distal side reinforcement 17 is disposed inside the inflatable portion 31 of the balloon 3 with the distal end approximately aligned with the distal end of the inflatable portion 31, and the proximal side reinforcement 18 is disposed inside the inflatable portion 31 of the balloon 3 with the proximal end approximately aligned with the proximal end of the inflatable portion 31. However, the reinforcements 17 and 18 may be disposed at a position a little distance inward to the middle of the inflatable portion 31. The reinforcements 17 and 18 may also be disposed so that they are partly covered by the corresponding bonding portions of the balloon 3. Further, the reinforcements 17 and 18 may be disposed so that they are partly covered by the corresponding bonding portions of the balloon 3 and the corresponding stoppers. The position of the distal end of the distal side reinforcement 17 is preferably within 3 mm on both sides from the distal end of the inflatable portion 31 of the balloon 3.

A distal portion of the reinforcement 17 mat be disposed so as to be covered by the distal bonding portion of the balloon 3. Further, the distal bonding portion of the balloon 3 covering with the distal portion of the reinforcement 17 may be covered by the distal side stopper 5. A proximal end portion of the proximal side reinforcement 18 may be located inside the distal end portion of the outer tube 13. The proximal end portion of the proximal side reinforcement 18 overlaps to the distal end portion of the proximal side stopper 6.

The reinforcements may be in the shape of a ring of a predetermined length or a wound coil of wire. The reinforcements is preferably made of an X-ray opaque material (gold, platinum, tungsten, or an alloy of them, or silver-palladium alloy, for example). By using an X-ray opaque material, the position of the distal and proximal ends of the inflatable portion 31 of the balloon 3, and hence the positions of the distal and proximal ends of the stent 4 can be known from the X-ray shadow of the reinforcements.

The stent 4 used for the stent delivery device 100 of this embodiment is the same as the one used for the previous embodiment.

A rigidity-imparting member 33 is inserted in the inner tube 12 and the outer tube 13 (in the balloon inflating lumen 16). The rigidity-imparting member 33 prevents too sharp bending of the main body 10 of the stent delivery device 100 at bent portions of blood vessels, and thereby facilitates the insertion of the distal end portion of the stent delivery device 100 through bent portions of blood vessels.

The rigidity-imparting member 33 is preferably a metal wire formed of an elastic metal (a stainless steel, etc.) or a super elastic alloy, within the range of 0.05 to 1.5 mm, preferably 0.1 to 1.0 mm in diameter. Wire of a high tensile strength stainless steel for spring or a super elastic alloy is particularly preferable. Of super elastic alloys, those described above are preferable.

The distal end portion of the rigidity-imparting member 33 is made smaller in diameter than the other portion by grinding, for example. In this embodiment, the distal end of the small-diameter portion is extended near the distal end portion 3b of the outer tube 13 of the main body. The distal end of the small-diameter portion may be extended near the distal end of the outer tube 13. The distal end of the rigidity-imparting member 33 is not secured to the outer tube 13 or the inner tube 12. The exterior diameter of the small-diameter portion of the rigidity-imparting member 33 is preferably within the range of about $1/10$ to $1/5$ of that of the proximal end portion. Further, the rigidity-imparting member 33 has preferably a higher rigidity in the proximal portion than in the distal portion. The rigidity-imparting member 33 can be endowed with such a rigidity by forming it so that the proximal portion has a larger cross-sectional area than the distal portion. It is also possible by cold-working a metal wire used for the rigidity-imparting member 33 and then annealing the wire with a temperature gradient high on the distal side and low on the proximal side. The rigidity-imparting member 33 may also be made of a stranded wire with several thin metal wires twisted.

The proximal end portion of the rigidity-imparting member 33 is secured to the proximal end of the inner tube 12. The proximal end portion of the rigidity-imparting member 33 may be secured to the proximal end of the outer tube 13. Since the rigidity-imparting member 33 is not secured at the other portion, it can move in the balloon inflating lumen 16 relative to the inner and outer tubes.

By adding such a rigidity-imparting member 33, the main body 10 of the stent delivery device can be prevented from meandering within a blood vessel. Therefore, the pushing force applied to the proximal end portion of the main body 10 is transmitted exactly to the distal end without being buffered by the meandering portion. This facilitates the insertion of the balloon-attached portion in the distal end portion of the stent delivery device into a stenosed part of a blood vessel, and further makes it possible to insert the distal end portion of the dilating device into a severely stenosed part (subtotally stenosed part).

Next, the proximal end portion of the stent delivery device 100 of this embodiment is described with reference to FIG. 12.

The stent delivery device 100 of this embodiment has a branched-hub 112 attached to the proximal end.

The branched-hub 112 consists of an inner-tube hub 122 which is attached to the inner tube 12 and has a guide wire introducing opening 109 communicating with the guide wire lumen 15 and serving as the guide wire port, and an outer-tube hub 123 which is attached to the outer tube 13 and has a balloon inflating liquid injection port 111 communicating with the balloon inflating lumen 16. The outer-tube hub 123 and the inner-tube hub 122 are connected together.

For the material for forming the branched-hub 112, thermoplastic resins such as polycarbonate, polyamide, polysulfone, polyacrylate, and methacrylate-butylene-styrene copolymer can be preferably used.

In this example, a kink-preventing tube 150 is fitted over the proximal end portion of the outer tube 13. The kink-preventing tube 150 is formed of a heat-shrinking material so as to have an interior diameter which becomes a little smaller than the exterior diameter of the outer tube 13 when it shrinks from heat. The kink-preventing tube 150 can be easily fitted over the proximal end of the outer tube 13 by sliding it over the proximal end of the outer tube 13 and heating it (by blowing hot air, for example).

The proximal end of the outer tube 13 with the kink-preventing tube 150 attached is secured to the outer-tube hub 123 by means of a retainer 152. The retainer 152 has a cylindrical portion with the exterior diameter approximately equal to the interior diameter of the outer tube 13 and a larger-diameter flared proximal end portion. The retainer 152 is inserted into the proximal end of the outer tube 13, and the outer tube 13 is inserted into the outer-tube hub 123 with the distal end leading until the flared distal end of the retainer 152 passes through a projection 154 formed in the inside surface of the outer-tube hub 123. An adhesive may be applied between the surfaces of the outer-tube hub 123 and the kink-preventing tube 150 to bond them.

A kink-preventing tube 160 is fitted over the proximal end portion of the inner tube 12. The kink-preventing tube 160 is formed of a heat-shrinking material so as to have an interior diameter which becomes a little smaller than the exterior diameter of the inner tube 12 when it shrinks from heat. The kink-preventing tube 160 can be easily fitted over the proximal end of the inner tube 12 by putting it on the proximal end of the inner tube 12 and heating it (by blowing hot air, for example).

The proximal end portion of the rigidity-imparting member 33 is secured to the outside surface of the inner tube 12 by this thermoshrinking tube 160. The inner tube 12 with the kink-preventing tube 160 attached is secured to the inner-tube hub 122 by means of a retainer 162. The retainer 162 has a cylindrical portion with the exterior diameter approximately equal to the interior diameter of the inner tube 12 and a larger-diameter flared proximal end portion. The retainer 162 is inserted into the proximal end of the inner tube 12, and the inner tube 12 is inserted into inner-tube hub 122 with the distal end leading until the flared distal end of the retainer 162 passes through a projection 164 formed in the inside surface of the inner-tube hub 122. An adhesive may be applied between the surfaces of the inner-tube hub 122 and the kink-preventing tube 160 to bond them.

The material for the outer-tube hub 123 and the inner-tube 122, thermoplastic resins such as polycarbonate, polyamide, polysulfone, polyacrylate, and methacrylate-butylene-styrene copolymer can be preferably used.

The inner-tube hub 122 and the outer-tube hub 123 are joined together. This joining is made by inserting the inner tube 12 with the distal end leading into the outer-tube hub 123 attached to the proximal end portion of the outer tube 13 from the proximal end, and then joining the outer-tube hub 123 and the inner-tube hub 122. The outer-tube hub 123 and the inner-tube hub 122 may be joined by applying an adhesive to their joined portions.

The structure of the proximal portion of the stent delivery device 100 is not limited to the one described above. Instead of the branched hub 112, tubes equipped with end pieces which have openings serving as ports in their proximal ends may be connected to the guide-wire lumen 15 and the balloon dilating lumen 16 in a liquid tight fashion.

Next, the stent delivery device 81 of another embodiment of this invention is described with reference to FIG. 13.

Figure 13:
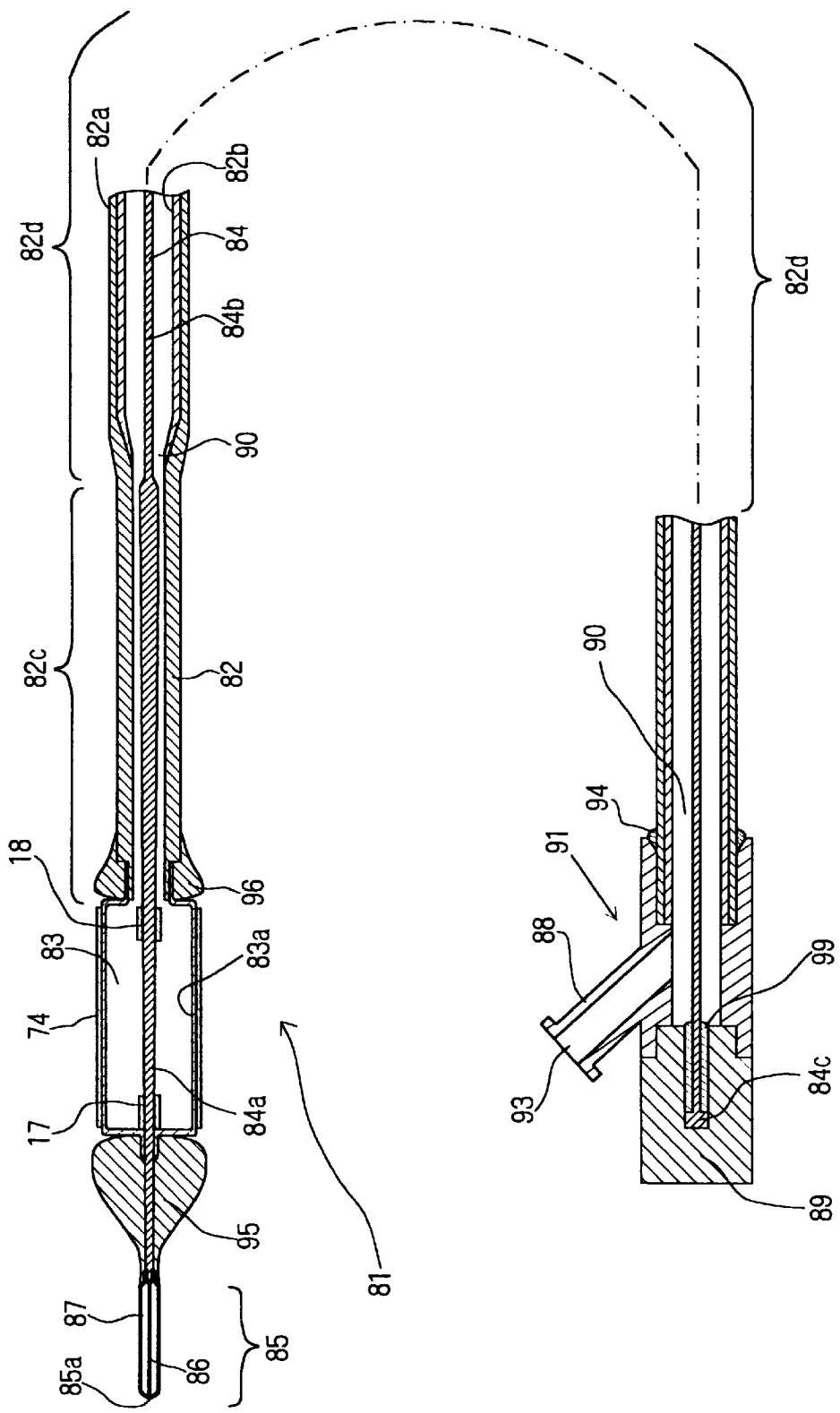
FIG. 13 is a sectional view of the distal and proximal end portions of another embodiment of the stent delivery device of this invention.

FIG. 13 is an enlarged partial sectional view of the stent delivery device of another embodiment of this invention.

In the stent delivery device 81 of this embodiment, the shaft body has a guiding portion 85 which extends beyond the distal end. The differences between the stent delivery device 81 and the above-described stent delivery device 1 shown in FIGS. 1 to 7 are only in the structure of the shaft body and the shape of the proximal side stopper 96. The other parts are the same.

This stent delivery device 81 comprises a shaft body, a dilating balloon attached to the distal end portion of the shaft body, and a stent 74 fitted over the balloon 83. The shaft body comprises a tubular body 82 which has a balloon inflating lumen 90 inside, a resilient core 84 extending through the tubular body 82 and the balloon 83, a guiding portion 85 connected to the distal end of the core 84, and a hub assembly 91.

The tubular body 82 of this stent delivery device 81 comprises an inner tube 82b and an outer tube 82a which envelopes the inner tube 81. The outer tube 82a extends beyond the distal end of the inner tube 82b and forms the distal end portion 82c of the tubular body 82.

Further, in the stent delivery device 81 of this embodiment, the outer tube 82a is tapered so as to become gradually smaller in exterior diameter toward the distal end in the portion which encloses the distal end portion of the inner tube 82b. The distal end portion of the inner tube 82b may be tapered so as to fit in the tapered portion of the outer tube 82a or may be deformed by the outer tube 82a. By making the distal end portion 82c of the tubular body 82, formed of the outer tube 82a alone without the inner tube 82b inside, smaller in exterior diameter than the main portion 82d of the tubular body 82, formed of the outer tube 82a and the inner tube 82b, it is made possible to insert the distal end portion of the stent delivery device 81 into thinner blood vessels. Further, by forming the transition region from the main portion 82d to the distal end portion 82c in the tubular body 82 so as to become smaller in exterior diameter in taper toward the distal end, insertion of the stent delivery device into a blood vessel is made easier.

Since the main portion 82d of the tubular body 82 of this stent delivery device 81 has the inner tube 82b, the capability of transmitting pushing motions applied to the proximal end portion of the dilating device (pushability) and that of transmitting turning motions around the axis applied to the distal end portion (torque transmitting capability) are considerably improved.

The distal end portion of the tubular body is formed of a synthetic resin.

The distal end of the tubular body 82 is receded a little distance from the distal end of the resilient core 84. The tubular body 82 is formed coaxial out of the resilient core 84.

The tubular body 82 is within the range of 100 to 4000 mm, more preferably 150 to 1600 mm in length, and within the range of 0.3 to 1.5 mm, more preferably 0.4 to 1.2 mm in exterior diameter.

For the material for forming the outer tube 82a, synthetic resins with an appropriate elasticity such as thermoplastic resins [polyolefin (polyethylene, polypropylene, ethylene-propylene copolymer, ethylene-vinyl acetate copolymer, etc.), poly(vinyl chloride), a polyamide elastomer, polyurethane, etc.] and polyamide are usable. Of these synthetic resins polyolefin and polyimide are preferable.

The wall thickness of the portion of the outer tube 82a with the inner tube 82b fitted in is within the range of 5 to 300 μm, preferably 10 to 200 μm.

A heat-shrinking tube may also be used for the outer tube 82a of the tubular body 82. A heat-shrinking tube, whose interior diameter before heating is a little larger than the exterior diameter of the inner tube 82b and in which the inner tube 82b can be inserted, and which shrinks uniformly from heating and tightly fits over the outside surface of the inner tube 82b, is used. Especially, a heat-shrinking tube, which is formed in an interior diameter equal to or a little smaller than the exterior diameter of the inner tube 82b and extended to an interior diameter a little larger than the exterior diameter of the inner tube 82b, and shrinks from heating to the interior diameter equal to or approximately equal to that of the tube when the tube is first formed, is preferably used.

For the material for the heat-shrinking tube, substances which can be extended in the manner as described above and shrinks from heating, such as polyolefin (polyethylene, polypropylene, ethylene-propylene copolymer, etc.), ethylene-vinyl acetate copolymer, and polyamide elastomer, are usable.

For the inner tube 82b, synthetic resins and elastic metals enumerated for the material for forming the outer tube of the previous embodiments are usable. When forming the inner tube of a synthetic resin, it is preferable to use a synthetic resin which has a higher hardness than the synthetic resin used for the outer tube. For the elastic metal, stainless steels and super elastic metals are preferable. For the super elastic metal, those described above are preferably used.

The inner tube 82b is within the range of 0.2 to 1.5 mm, preferably 0.3 to 1.2 mm in exterior diameter, and within the range of 30 to 200 μm, preferable 50 to 150 μm in wall thickness. The buckling strength (yielding stress when subjected to a compressive load) of the inner tube 82b is within the range of 5 to 200 kg/mm$^2$ (22° C.), preferably 8 to 150 kg/mm$^2$ (22° C.). The restoring stress (yielding stress when a load is removed) is within the range of 3 to 180 kg/mm$^2$ (22° C.), preferably 5 to 130 kg/mm$^2$ (22° C.).

The resilient core 84 is extended through the tubular body 82, and has a guiding portion 85 secured to the distal end. Specifically, a guiding portion 85 made of a coil spring 87 is attached to the distal end of the resilient core 84. The distal end of the coil spring 87 is confined with a wire 86 stretched inside the coil spring 87 so as to prevent the coil spring 87 from being drawn. The distal and proximal ends of the wire 86 is secured to the opposite ends of the coil spring 87.

It is preferable that the distal portion of the resilient core 84 becomes more flexible toward the distal end. Therefore, the distal portion of the resilient core 84 is formed so as to become gradually smaller in exterior diameter toward the distal end. Further, in this embodiment, the proximal portion of the distal portion 84a of the resilient core 84, which is covered by the distal end portion 82c of the tubular body 82, has a larger diameter than the proximal portion 84b of the resilient core 84 covered by the main portion 82d of the tubular body 82, in order to prevent the distal end portion 82c of the tubular body 82 (the portion consisting of the outer tube alone) from buckling.

For the material for the resilient core 84, stainless steels (preferably a high tensile strength stainless steel for spring), tungsten, tungsten-cobalt alloys, piano wire (preferably piano wire plated with Nickel or Chromium), and super elastic alloys are usable. Of super elastic alloys, those described above are preferable.

The length of the resilient core 84 is within the range of 350 to 4000 mm, preferably 550 to 1800 mm. The buckling strength (yielding stress when subjected to a compressive load) of the resilient core 84 is within the range of 30 to 100 kg/mm$^2$ (22° C.), preferably 40 to 55 kg/mm$^2$ (22° C.). The restoring stress (yielding stress when a load is removed) is within the range of 20 to 80 kg/mm$^2$ (22° C.), preferably 30 to 35 kg/mm$^2$ (22° C.). The example of the distal end portion of the resilient core 84 is within the range of 0.1 to 1.0 mm, preferably 0.15 to 0.7 mm. The bending load is within the range of 0.1 to 10 g, preferably 0.3 to 6.0 g. The restoring load is 0.1 to 10 g, preferably 0.3 to 6.0 g.

The guiding portion 85 performs the function of guiding the stent delivery device 81 to the aimed part of a blood vessel and consists of a coil spring 87. This guiding portion 85 has a flexibility such that when the distal end of the guiding portion 85 comes into contact with the wall of a blood vessel, it easily bends to change the direction of advance without causing a concentration of the pressing force. Further, since the guiding portion 85 is also the distal end portion of the stent delivery device 81, it is preferable that the position of the guiding portion 85 can be easily viewed with fluoroscopy. For the material for the guiding portion 85, Plutonium, Plutonium alloys, Tungsten, Tungsten alloys, Silver, and Silver alloys, for example, are preferable.

To endow the guiding portion 85 with a higher flexibility, the coil spring 87 may also be formed of a wire of a super elastic metal (super elastic alloy) or an elastic metal.

The coil spring 87 is preferably within the range of 0.2 to 1.0 mm in exterior diameter and within the range of 2 to 50 mm in length.

When forming the guiding portion 85 of a super elastic metal wire, the buckling strength (yielding stress when subjected to a compressive load) is within the range of 5 to 200 kg/mm$^2$ (22° C.), preferably 8 to 150 kg/mm$^2$ (22° C.). The restoring stress (yielding stress when a load is removed) is within the range of 3 to 180 kg/mm$^2$ (22° C.), preferably 5 to 150 kg/mm$^2$ (22° C.).

The distal end 85a is preferably formed in the shape of a headpiece having a smooth convex surface by fusing coils of very thin metal wire. The coil spring 87, which constitutes the guiding portion 85, and the resilient core 84 are joined by brazing. It is also possible to extend the distal end of the resilient core 84 to the distal end of the guiding portion 85 and connect the extended distal end to the distal end of the coil spring 87 instead of using a wire to prevent the coil spring 87 from being drawn.

The balloon 83 has a distal side bonding portion and a proximal side bonding portion. The distal side bonding portion is bonded to the resilient core 84 at a position a little distance proximal from the distal end of the resilient core 84, and the proximal side bonding portion is bonded to the distal end portion of the tubular body 82. The balloon 83 communicates with the balloon inflating lumen 90 (inside of the tubular body 82) near its proximal end.

A distal side stopper 95 is attached to the distal end portion of the resilient core 84 between the distal end of the balloon 83 and the proximal end of the guiding portion 85 so as to cover the distal end portion of the distal side bonding portion of the balloon 83. That entire the distal side bonding portion of the balloon 83 is covered with the distal side stopper 95 is desirable. The distal side stopper 95 is formed of an elastic material in a ring-like shape with the exterior diameter of the proximal end portion approximately equal to or a little larger than the exterior diameter of the stent 74. The distal side stopper 95 is tapered so as to become gradually smaller in exterior diameter toward the distal end.

A proximal said stopper 96, formed of an elastic material, is attached to the distal end portion of the tubular body 82 so as to cover the proximal end portion of the proximal side bonding portion of the balloon 83. That entire the proximal side bonding portion 3b of the balloon 3 is covered with the proximal side stopper 6 is desirable. The proximal side stopper 96 also has an exterior diameter approximately equal to or a little larger than that of the stent 74. Similarly to the distal side stopper 95, the proximal side stopper 96 is tapered so as to become gradually smaller in exterior diameter toward the proximal end (in the direction away from the balloon 3).

The stent 74 is held between these two stoppers, and its move beyond the stoppers is prevented. The distal end of the stent 74 is close to the distal side stopper 95, and the proximal end of the stopper 74 to the proximal side stopper 96. Therefore, the edges in both ends of the stent 74 do not come into contact with the inside surface of bodily organs (inside surface of blood vessels, for example) when the stent delivery device is being inserted. Therefore, infliction of injuries on the inside wall of body organs by the edges of the stent can be prevented.

For the material for forming the stoppers, substances with an appropriate elasticity including thermoplastic resins [polyolefins (polyethylene, polypropylene, ethylene-propylene copolymer, ethylene-vinyl acetate copolymer, etc.), poly(vinyl chloride), polyamide elastomer, polyurethane, etc.], silicone rubber, and latex rubber, for example, are usable. The thermoplastic resins as described above are preferable, and polyolefins are particularly preferable.

The balloon 83 is foldable, and folded so as to fit over the outside surface of the resilient core 84. The balloon 83 has an inflatable portion 83a in the shape of a cylinder (preferably circular cylinder) with an approximately uniform exterior diameter for expanding the stent 74. The shape of the inflatable portion 83 need not be a circular cylinder, and may be a polygonal cylinder, for example. The balloon 83 is attached to the dilating device by bonding the distal side bonding portion to the resilient core 84 and the proximal side bonding portion to the distal end portion of the tubular body 82 in the liquid-tight fashion by an adhesive or welding. Further, the balloon 83 is a taper-less balloon which does not have a tapered portion formed between the inflatable portion 83a and each of bonding portions. Therefore, the distal side stopper 95 is disposed on the shaft body (resilient core 84, to be exact) close to the distal end of the inflatable 83a of the balloon 83. Similarly, the proximal side stopper 96 is disposed on the shaft body (outer tubular body 82, to be exact) close to the proximal end of the inflatable portion 83a of the balloon 83.

The balloon 83 forms an inside space 92 between its inside surface and the outside surface of the resilient core 84. This inside space communicates with the balloon inflating lumen 90 (inside of the tubular body 82) on entire circumference at its proximal end portion.

The size and material of the balloon 83 is the same as those described above.

A distal side reinforcement 17 is attached to the outside surface of the shaft body (resilient core 84 in this embodiment) at a position which is close to the distal side stopper 95 and also close to the distal end of and inside the inflatable portion 83a. Similarly, a proximal side reinforcement 18 is attached to the outside surface of the shaft body (tubular body 82 in this embodiment) at a position which is close to the proximal side stopper 96 and also close to the proximal end of and inside the inflatable portion 83a. By adding such reinforcements, kinking of the dilating device between each stopper and the stent 74 can be prevented.

The distal end of the distal side reinforcement 17 is preferably located on the distal side of the distal end of the above-described stent 74, and the proximal end of the proximal side reinforcement 18 preferably on the proximal side of the proximal end of the stent 74. The proximal portion of the distal side reinforcement 17 is preferably located inside the stent 74. The distal end portion of the proximal side reinforcement 18 is preferably located inside the stent 74. The outer edge of the distal end of the distal side reinforcement 17 is preferably rounded. The outer edges of the distal and proximal ends of the distal side reinforcement 17 is more preferably rounded. The outer edges oft he distal and proximal ends of the proximal side reinforcement 18 is preferably rounded.

In this embodiment, the distal side reinforcement 17 is disposed inside the inflatable portion 83a of the balloon with the distal end approximately aligned with the distal end of the inflatable portion 83a, and the proximal side reinforcement 18 is located inside the inflatable portion 83a with the proximal end approximately aligned with the proximal end of the inflatable portion 83a. However, the reinforcements 17 and 18 may be disposed a little distance inward to the middle of the inflatable portion 31. The reinforcements 17 and 18 may also be disposed so that they are partly covered by the corresponding bonding portions of the balloon 83. Further, the reinforcements 17 and 18 may be disposed so that they are partly covered by the corresponding bonding portions of the balloon 83 and the corresponding stoppers. The position of the distal end of the distal side reinforcement 17 is preferably within 3 mm on both sides from the distal end of the inflatable portion 83a of the balloon 83.

A distal portion of the reinforcement 17 mat be disposed so as to be covered by the distal bonding portion of the balloon 83. Further, the distal bonding portion of the balloon 83 covering with the distal portion of the reinforcement 17 may be covered by the distal side stopper 95. A proximal end portion of the proximal side reinforcement 18 may be located inside the distal end portion of the outer tube 82. The proximal end portion of the proximal side reinforcement 18 overlaps to the distal end portion of the proximal side stopper 96.

The reinforcements may be a ring of an appropriate length or a coil of wire. Further, its is preferable to form the reinforcements of an X-ray opaque material (gold, platinum, tungsten, an alloy of them, or silver-palladium alloy, for example). By using an X-ray opaque material, the positions of the distal and proximal ends of the inflatable portion 83a of the balloon, and hence the positions of the distal and proximal ends of the stent 74 can be viewed with fluoroscopy.

The stent 74 used with this stent delivery device is the same as that described above.

The hub assembly 91 consists of a branched tubular-body hub 88 and a resilient-core hub 89. The tubular-body hub 88 is connected to the proximal end portion of the tubular body 82 by an adhesive 94. The tubular-body hub 88 has an opening 93 which communicates with the lumen 90. The opening 93 constitutes the balloon inflating liquid injecting port. For the material for the hub 88, thermoplastic resins such as polyolefins (polypropylene, polyethylene, etc.), polycarbonate, polyamide, polysulfone, polyacrylate, butylene-stylene copolymer, and methacrylate-butylene-stylene copolymer can be used.

The resilient-core hub 89 has a cylinder hole which can receive the enlarged-diameter portion 84c formed at the proximal end of the resilient core 84. The proximal end portion of the resilient core 84 is inserted in the hold of the resilient-core hub 89. The resilient core 84 and the resilient-core hub 89 are secured by an adhesive 99. Further, the tubular-body hub 88 and the resilient-core hub 89 are joined together, by fitting the distal end of the resilient-core hub 89 in the proximal end of the tubular-body hub 88, as shown in FIG. 13. By applying an adhesive to the portions joined, the tubular-body hub 88 and the resilient-core hub 89 are firmly secured.

Further, the stent delivery devices of the above-described all embodiments are preferably treated to increase the lubricity on the outside surface of the shaft body, the outside surface of its distal end portion (that is, the portion from the distal side stopper to the distal end), and the outside surface of the proximal side stopper in order to facilitate their insertion into blood vessels or a guiding catheter. The treatment can be performed by coating the outside surfaces of those portions with a substance which reduces friction such as a hydrophilic polymer [poly(2-hydroxyethyl-methacrylate), polyhydroxy-ethylacrylate, hydroxypropylcellulose, methyl vinyl ether maleic anhydride copolymer, polyethylene glycol, polyacrylamide, polyvinylpyrrolidone, etc.] or reactive silicone resin having polydimethylsiloxane as the main chain, or by fixing the same substance on the surfaces of those portions.

Since the stent delivery device of this invention has the structure as described above, the stent fitted over the balloon rarely move from the original position, or if the stent happens to shift a little, both ends of the stent are still located over the inflatable portion of the balloon which is inflated into the shape of a uniform-diameter cylinder. Therefore, the stent delivery device of this invention can expand the entire stent completely into the intended shape without causing incomplete expansion at either end portion.

What is claimed is:

1. A stent delivery device comprising, a tubular shaft body, a foldable and inflatable balloon attached to a distal end portion of the shaft body, and a stent fitted over the balloon and being expandable by inflation of the balloon, said shaft body having a lumen for inflating said balloon, said balloon having an inflatable portion which is inflatable into a shape of an approximately uniform-diameter cylinder by a fluid injected through said lumen, a distal side stopper for preventing a shift of said stent toward a distal side of the shaft body, said distal side stopper being secured to said shaft body close to a distal end of said inflatable portion of said balloon, a proximal side stopper for preventing a shift of said stent toward a proximal side of the shaft body, said proximal side stopper being secured to said shaft body close to a proximal end of said inflatable portion of said balloon; and a reinforcement secured to an outside surface of said shaft body, said reinforcement having a distal end aligned with or near the distal end of said inflatable portion of said balloon, said reinforcement being located at least partially inside said balloon, said distal end of the reinforcement being located on the distal side of said shaft body from a distal end of the stent, a proximal portion of the reinforcement being located inside the stent, said reinforcement having a finite length defined by said distal end and a proximal end of said reinforcement, said proximal end of said reinforcement being located inside said stent.

2. A stent delivery device of claim 1, wherein said balloon has a distal side bonding portion for attaching the balloon to said shaft body, and said distal side stopper is disposed so as to cover the distal side bonding portion of said balloon.

3. A stent delivery device of claim 1, wherein said balloon has a proximal side bonding portion for attaching the balloon to said shaft body, and said distal side stopper is disposed so as to cover the distal side bonding portion of said balloon.

4. A stent delivery device of claim 1, wherein said balloon does not include taper inflatable portions on a distal side of said inflatable portion of said balloon and on a proximal side of said inflatable portion of said balloon.

5. A stent delivery device of claim 1, wherein said distal side stopper is tapered so as to become gradually smaller in diameter toward a distal end of the shaft body.

6. A stent delivery device of claim 1, wherein said proximal side stopper is tapered so as to become gradually smaller in diameter toward a proximal end of the shaft body.

7. A stent delivery device of claim 1, wherein said distal side stopper and said proximal side stopper are formed in the shape of a ring and have exterior diameters approximately equal to or larger than an exterior diameter of said stent fitted over said folded balloon.

8. A stent delivery device of claim 1, wherein the stent delivery device has a proximal side reinforcement secured to the outside surface of said shaft body, said proximal side having a proximal end aligned with or near the proximal end of said inflatable portion of said balloon, said proximal side reinforcement being located at least partially inside said balloon.

9. A stent delivery device of claim 8, wherein the proximal end of said proximal side reinforcement is located on said proximal side of said shaft body from a proximal end of said stent, a distal end portion of said proximal side reinforcement being located inside said stent.

10. A stent delivery device of claim 1, wherein said shaft body has a lumen for passing a guide wire through, said lumen being open at the distal end of said shaft body.

11. A stent delivery device of claim 1, wherein said shaft body has a lumen for passing a guide wire through, said lumen having a first open end at a distal end of said shaft body and a second open end in a middle part of the shaft body.

12. A stent delivery device of claim 1, wherein said shaft body has a lumen for passing a guide wire through, said lumen having a first end that is open at a distal end of said shaft body and a second end that is open at a proximal end of the shaft body.

13. A stent delivery device of claim 1, wherein said shaft body has a resilient core which extends from a proximal end of said shaft body to a distal end of said shaft body, said resilient core being located inside said shaft body, and a guiding portion which extends beyond the distal end of said shaft body.

14. A stent delivery device of claim 1, wherein said reinforcement contacts the distal end of said inflatable portion of said balloon.

15. A stent delivery device of claim 1, wherein a proximal end portion of said reinforcement is covered by a distal bonding portion of the balloon.

16. A stent delivery device of claim 1, wherein a position of said distal end of said reinforcement is within 3 mm from said distal end of said inflatable portion of said balloon.

17. A stent delivery device of claim 1, wherein said reinforcement is a first reinforcement, said first reinforcement having a finite length defined by said distal end of said first reinforcement and a proximal end of said first reinforcement, said proximal end of said first reinforcement being located inside said inflatable portion, further comprising a second reinforcement secured to an outside surface of said shaft body, said second reinforcement having a finite length defined by a distal end of said second reinforcement and a proximal end of said second reinforcement, said proximal end of said second reinforcement being aligned with or near said proximal end of said inflatable portion of said balloon, said second reinforcement being located at least partially inside said balloon, said proximal end of said second reinforcement being located on said proximal side of said shaft body from a proximal end of said stent, a distal end of said second reinforcement being located inside said stent.

18. A stent delivery device comprising, a tubular shaft body having a distal end, a proximal end, and a distal end portion;

a foldable and inflatable balloon attached to said distal end portion of said shaft body, said inflatable balloon having an inflatable portion inflatable into a shape of an approximately uniform-diameter cylinder, said inflatable portion having a distal end portion and a proximal end portion;

a stent fitted over said folded balloon and being expandable by inflation of said balloon, said shaft body having a lumen for inflating said balloon;

a distal side stopper for preventing shifting of said stent in a direction toward said distal end of said shaft body, said distal side stopper being secured to said shaft body substantially at said distal end portion of said inflatable portion of said balloon;

a proximal side stopper for preventing shifting of said stent in a direction toward said proximal end of said shaft body, said proximal side stopper being secured to said shaft body substantially at said proximal end portion of said inflatable portion of said balloon;

a first reinforcement secured to an outside surface of said shaft body, said first reinforcement having a finite length defined by a distal end and a proximal end of said first reinforcement, said distal end of said first reinforcement being aligned with or near said distal end portion of said inflatable portion of said balloon, said first reinforcement being located at least partially inside said balloon, said distal end of said first reinforcement being located on a distal side of a distal end of said stent, said proximal end of said first reinforcement being located inside said stent; and a second reinforcement secured to said outside surface of said shaft body, said second reinforcement having a finite length defined by a distal end and a proximal end of said second reinforcement, said proximal end of said second reinforcement being aligned with or near said proximal end portion of said inflatable portion of said balloon, said second reinforcement being located at least partially inside said balloon, said proximal end of said second reinforcement being located on a proximal side of a proximal end of said stent, said distal end of said second reinforcement being located inside said stent.

19. A stent delivery device comprising, a tubular shaft body having a distal end, a proximal end, and a distal end portion;

a foldable and inflatable balloon attached to said distal end portion of said shaft body, said inflatable balloon having an inflatable portion inflatable into a shape of an approximately uniform-diameter cylinder, said inflatable portion having a distal end portion and a proximal end portion;

a stent fitted over said folded balloon and being expandable by inflation of said balloon, said shaft body having a lumen for inflating said balloon;

a distal side stopper for preventing shifting of said stent in a direction toward said distal end of said shaft body, said distal side stopper being secured to said shaft body substantially at said distal end portion of said inflatable portion of said balloon;

a proximal side stopper for preventing shifting of said stent in a direction toward said proximal end of said shaft body, said proximal side stopper being secured to said shaft body substantially at said proximal end portion of said inflatable portion of said balloon;

a first reinforcement secured to an outside surface of said shaft body, said first reinforcement having a finite length defined by a distal end and a proximal end of said first reinforcement, said distal end being aligned with or near said distal end portion of said inflatable portion of said balloon, said first reinforcement being located at least partially inside said balloon, said distal end of said first reinforcement being located on a distal side inside said stent; and a second reinforcement secured to said outside surface of said shaft body, said second reinforcement having a finite length defined by a distal end and a proximal end of said second reinforcement, said proximal end of said second reinforcement being aligned with or near said proximal end portion of said inflatable portion of said balloon, said second reinforcement being located at least partially inside said balloon, said proximal end of said second reinforcement being located on a proximal side of a proximal end of said stent, said distal end of said second reinforcement being located inside said stent.

* * * * *

UNITED STATES PATENT AND TRADEMARK OFFICE
CERTIFICATE OF CORRECTION

PATENT NO. : 6,106,530
DATED : August 22, 2000
INVENTOR(S) : Kinya Harada

It is certified that error appears in the above-identified patent and that said Letters Patent is hereby corrected as shown below:

Column 17,
Line 56, insert -- portion -- between "inflatable" and "83a".

Column 18,
Line 23, delete "oft he" and insert -- of the --.

Column 22,
Line 15, delete "comprising," and insert therefor -- of claim 1, wherein said reinforcement is only located between said distal side stopper and said proximal side stopper. --
Line 16-58, delete in their entirety.

Signed and Sealed this

Ninth Day of October, 2001

Attest:

NICHOLAS P. GODICI
Attesting Officer
Acting Director of the United States Patent and Trademark Office